(12) United States Patent
Girotra et al.

(10) Patent No.: US 10,632,017 B2
(45) Date of Patent: *Apr. 28, 2020

(54) TRIGGER ASSEMBLY FOR TYMPANOSTOMY TUBE DELIVERY DEVICE

(71) Applicant: Tusker Medical, Inc., Menlo Park, CA (US)

(72) Inventors: Rohit Girotra, San Francisco, CA (US); Thomas D. Gross, Los Gatos, CA (US)

(73) Assignee: TUSKER MEDICAL, INC., Menlo Park, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 15/426,681

(22) Filed: Feb. 7, 2017

(65) Prior Publication Data

US 2017/0209310 A1    Jul. 27, 2017

Related U.S. Application Data

(63) Continuation of application No. PCT/US2015/044179, filed on Aug. 7, 2015, which is
(Continued)

(51) Int. Cl.
*A61F 11/00* (2006.01)
*A61B 17/34* (2006.01)
*A61B 90/00* (2016.01)

(52) U.S. Cl.
CPC ........ *A61F 11/002* (2013.01); *A61B 17/3415* (2013.01); *A61B 17/3468* (2013.01); *A61B 2090/038* (2016.02)

(58) Field of Classification Search
CPC .............. A61F 11/002; A61B 17/3415; A61B 17/3468; A61B 2090/038
See application file for complete search history.

(56) References Cited

U.S. PATENT DOCUMENTS

| | | |
|---|---|---|
| 858,673 A | 7/1907 | Roswell |
| 1,920,006 A | 7/1933 | Dozier et al. |

(Continued)

FOREIGN PATENT DOCUMENTS

| | | |
|---|---|---|
| CN | 86105171 A | 3/1987 |
| CN | 2635015 Y | 8/2004 |

(Continued)

OTHER PUBLICATIONS

International Search Report for International Application No. PCT/US2008/060779, dated Sep. 3, 2008.

(Continued)

*Primary Examiner* — Richard G Louis

(57) ABSTRACT

A tympanostomy tube delivery device comprises a shaft assembly, a pressure equalization tube, and a trigger assembly. The shaft assembly comprises a cannula and a pusher operable to translate relative to the cannula. The pressure equalization tube is positioned within the shaft assembly. The pusher is operable to drive the pressure equalization tube out of the shaft assembly. The trigger assembly includes a pair of pushbuttons and a linkage. The pushbuttons are secured to the device via living hinges and are selectively pivotable. The linkage is configured to engage the delivery device to thereby selectively prevent actuation of the delivery device. The pivoting of one or both the pushbuttons is configured cause the linkage to collapse so as to disengage the delivery device and thereby actuate the delivery device.

20 Claims, 26 Drawing Sheets

Related U.S. Application Data a continuation of application No. 14/457,412, filed on Aug. 12, 2014, now Pat. No. 9,539,146, which is a continuation-in-part of application No. 12/836,654, filed on Jul. 15, 2010, now Pat. No. 8,864,774.

(60) Provisional application No. 61/225,893, filed on Jul. 15, 2009.

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,964,850 A | 10/1990 | Bouton et al. |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,810,848 A | 9/1998 | Hayhurst |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,248,112 B1 | 6/2001 | Gambale et al. |
| 6,251,121 B1 | 6/2001 | Saadat |
| 6,258,067 B1 | 7/2001 | Hill |
| D450,843 S | 11/2001 | McGuckin, Jr. et al. |
| 6,319,199 B1 | 11/2001 | Sheehan et al. |
| 6,358,231 B1 | 3/2002 | Schindler et al. |
| 6,398,758 B1 | 6/2002 | Jacobsen et al. |
| 6,416,512 B1 | 7/2002 | Ellman et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| 7,909,220 B2 | 3/2011 | Viola |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 9,681,891 B2 | 6/2017 | Andreas et al. |
| 9,707,131 B2 | 7/2017 | Shahoian |
| 9,770,366 B2 | 9/2017 | Liu et al. |
| 9,833,359 B2 | 12/2017 | Clopp |

(56) References Cited

U.S. PATENT DOCUMENTS

| | | | |
|---|---|---|---|
| 9,833,360 | B2 | 12/2017 | Andreas et al. |
| 9,833,601 | B2 | 12/2017 | Clifford |
| 10,130,515 | B2 | 11/2018 | Kaplan et al. |
| 10,195,086 | B2 | 2/2019 | Van et al. |
| 10,219,950 | B2 | 3/2019 | Andreas et al. |
| 10,258,776 | B2 | 4/2019 | Clifford et al. |
| 2001/0020173 | A1 | 9/2001 | Klumb et al. |
| 2002/0026125 | A1 | 2/2002 | Leysieffer |
| 2002/0069883 | A1 | 6/2002 | Hirchenbain |
| 2002/0111585 | A1 | 8/2002 | Lafontaine |
| 2002/0138091 | A1 | 9/2002 | Pflueger |
| 2002/0161379 | A1 | 10/2002 | Kaplan et al. |
| 2002/0169456 | A1 | 11/2002 | Tu et al. |
| 2003/0018291 | A1 | 1/2003 | Hill et al. |
| 2003/0040717 | A1 | 2/2003 | Saulenas et al. |
| 2003/0060799 | A1 | 3/2003 | Arenberg et al. |
| 2003/0097178 | A1 | 5/2003 | Roberson et al. |
| 2003/0120292 | A1 | 6/2003 | Park et al. |
| 2003/0187456 | A1 | 10/2003 | Perry |
| 2003/0199791 | A1 | 10/2003 | Boecker et al. |
| 2004/0054339 | A1 | 3/2004 | Ciok et al. |
| 2004/0064024 | A1 | 4/2004 | Sommer |
| 2005/0033343 | A1 | 2/2005 | Chermoni |
| 2005/0070765 | A1 | 3/2005 | Abdelgany et al. |
| 2005/0165368 | A1* | 7/2005 | Py .................. A61F 9/0008 604/289 |
| 2005/0182385 | A1 | 8/2005 | Epley |
| 2005/0187546 | A1 | 8/2005 | Bek et al. |
| 2005/0203552 | A1 | 9/2005 | Laufer et al. |
| 2005/0235422 | A1 | 10/2005 | Wallace |
| 2005/0240147 | A1 | 10/2005 | Makower et al. |
| 2006/0004323 | A1 | 1/2006 | Chang et al. |
| 2006/0095050 | A1 | 5/2006 | Hartley et al. |
| 2006/0142700 | A1 | 6/2006 | Sobelman et al. |
| 2006/0155304 | A1 | 7/2006 | Kaplan et al. |
| 2006/0161218 | A1 | 7/2006 | Danilov |
| 2006/0163313 | A1 | 7/2006 | Larson |
| 2006/0282062 | A1 | 12/2006 | Ishikawa et al. |
| 2007/0088247 | A1 | 4/2007 | Bliweis et al. |
| 2007/0233222 | A1 | 10/2007 | Roeder et al. |
| 2007/0276466 | A1 | 11/2007 | Lavelle et al. |
| 2008/0027423 | A1 | 1/2008 | Choi et al. |
| 2008/0051804 | A1 | 2/2008 | Cottler et al. |
| 2008/0065011 | A1 | 3/2008 | Marchand et al. |
| 2008/0083813 | A1* | 4/2008 | Zemlok .............. A61B 17/2909 227/181.1 |
| 2008/0212416 | A1 | 9/2008 | Polonio et al. |
| 2008/0262468 | A1 | 10/2008 | Clifford et al. |
| 2008/0262508 | A1 | 10/2008 | Clifford et al. |
| 2008/0262510 | A1 | 10/2008 | Clifford |
| 2009/0163828 | A1 | 6/2009 | Turner et al. |
| 2009/0171271 | A1 | 7/2009 | Webster et al. |
| 2009/0209972 | A1 | 8/2009 | Loushin et al. |
| 2009/0299344 | A1 | 12/2009 | Lee et al. |
| 2009/0299379 | A1* | 12/2009 | Katz .................. A61F 11/002 606/109 |
| 2009/0299433 | A1 | 12/2009 | Lee |
| 2010/0041447 | A1 | 2/2010 | Graylin |
| 2010/0048978 | A1 | 2/2010 | Sing et al. |
| 2010/0061581 | A1 | 3/2010 | Soetejo et al. |
| 2010/0160819 | A1 | 6/2010 | Parihar et al. |
| 2010/0198135 | A1 | 8/2010 | Morriss et al. |
| 2010/0217296 | A1 | 8/2010 | Morriss et al. |
| 2010/0274188 | A1 | 10/2010 | Chang et al. |
| 2010/0324488 | A1 | 12/2010 | Smith |
| 2011/0015645 | A1 | 1/2011 | Liu et al. |
| 2011/0022069 | A1 | 1/2011 | Mitusina |
| 2011/0077579 | A1 | 3/2011 | Harrison et al. |
| 2011/0288559 | A1 | 11/2011 | Shahoian |
| 2012/0074200 | A1 | 3/2012 | Schmid et al. |
| 2012/0130252 | A1 | 5/2012 | Pohjanen et al. |
| 2012/0179187 | A1 | 7/2012 | Loushin et al. |
| 2012/0265097 | A1 | 10/2012 | Melchiorri et al. |
| 2012/0283563 | A1 | 11/2012 | Moore et al. |
| 2012/0310145 | A1 | 12/2012 | Clifford et al. |
| 2013/0030456 | A1 | 1/2013 | Assell et al. |
| 2013/0090544 | A1 | 4/2013 | Clifford et al. |
| 2013/0338678 | A1 | 12/2013 | Loushin et al. |
| 2014/0094733 | A1 | 4/2014 | Clopp et al. |
| 2014/0100584 | A1 | 4/2014 | Konstorum et al. |
| 2014/0194891 | A1 | 7/2014 | Shahoian |
| 2014/0276906 | A1 | 9/2014 | Andreas et al. |
| 2014/0277050 | A1 | 9/2014 | Andreas et al. |
| 2015/0142029 | A1 | 5/2015 | Fahn et al. |
| 2015/0164695 | A1 | 6/2015 | Liu et al. |
| 2015/0209509 | A1 | 7/2015 | O'Cearbhaill et al. |
| 2015/0305944 | A1 | 10/2015 | Kaplan et al. |
| 2015/0320550 | A1 | 11/2015 | Downing et al. |
| 2016/0038341 | A1 | 2/2016 | Clopp et al. |
| 2016/0038342 | A1 | 2/2016 | Van et al. |
| 2016/0045369 | A1 | 2/2016 | Clopp |
| 2016/0045370 | A1 | 2/2016 | Andreas et al. |
| 2016/0045371 | A1 | 2/2016 | Girotra et al. |
| 2016/0213519 | A1 | 7/2016 | Andreas et al. |
| 2017/0281230 | A1 | 10/2017 | Andreas et al. |
| 2018/0055693 | A1 | 3/2018 | Liu et al. |
| 2018/0085258 | A1 | 3/2018 | Andreas et al. |
| 2018/0085563 | A1 | 3/2018 | Clifford et al. |
| 2018/0116876 | A1 | 5/2018 | Clopp |
| 2018/0304059 | A1 | 10/2018 | Clifford et al. |
| 2019/0083318 | A1 | 3/2019 | Kaplan et al. |
| 2019/0201242 | A1 | 7/2019 | Andreas et al. |

FOREIGN PATENT DOCUMENTS

| | | |
|---|---|---|
| CN | 1933761 A | 3/2007 |
| CN | 102122067 A | 7/2011 |
| CN | 102510746 A | 6/2012 |
| CN | 102920491 A | 2/2013 |
| CN | 103327881 A | 9/2013 |
| CN | 107072690 A | 8/2017 |
| DE | 19618585 | 11/1997 |
| DE | 19918288 A1 | 10/2000 |
| EP | 0214527 A1 | 3/1987 |
| FR | 2528656 | 11/1983 |
| JP | H 07-116190 A | 5/1995 |
| JP | 2012-533359 A | 12/2012 |
| JP | 2013-543396 A | 12/2013 |
| TW | 201200098 A | 1/2012 |
| WO | WO 1999/011175 A1 | 3/1999 |
| WO | WO 1999/017825 | 4/1999 |
| WO | WO 2001/028407 | 4/2001 |
| WO | WO 2002/056756 | 7/2002 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 2011/008948 | 1/2011 |
| WO | WO 2012/040430 | 3/2012 |
| WO | WO 2012/040600 | 3/2012 |
| WO | WO 2012/054934 | 4/2012 |
| WO | WO 2014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

Written Opinion for International Application No. PCT/US2008/060779, dated Sep. 3, 2008.
International Preliminary Report on Patentability for International Application No. PCT/US2008/060779, dated Nov. 17, 2009.
International Search Report for International Application No. PCT/US2009/052395, dated Nov. 6, 2009.
Written Opinion for International Application No. PCT/US2009/052395, dated Nov. 6, 2009.

(56) References Cited

OTHER PUBLICATIONS

International Search Report for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
Office Action for Canadian Application No. 2,768,009, dated Aug. 4, 2016, 4 pages.
First Office Action for Chinese Application No. 201080041755.6, dated Jul. 3, 2013.
Notification of Reasons for Refusal for Japanese Application No. 2012-520778, dated Feb. 18, 2014.
Office Action for Korean Application No. 10-2012-7003590, dated Sep. 27, 2016, 9 pages.
Communication of the Substantive Examination Report for Mexican Application No. MX/a/2012/000691, dated Apr. 24, 2014.
Office Action for U.S. Appl. No. 12/836,654, dated Sep. 28, 2012, 16 pages.
Office Action for U.S. Appl. No. 12/836,654, dated Mar. 1, 2013, 23 pages.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
Office Action for U.S. Appl. No. 14/457,412, dated Mar. 25, 2016, 8 pages.
International Search Report and Written Opinion for International Patent Application No. PCT/US2015/044179, dated Dec. 18, 2015, 15 pages.
Office Action for U.S. Appl. No. 14/570,157, dated Jun. 15, 2016, 6 pages.
Office Action for U.S. Appl. No. 14/570,157, dated Jan. 20, 2016, 5 pages.
International Search Report and Written Opinion for International Application No. PCT/US2014/018320, dated Jun. 2, 2014, 10 pages.
International Search Report and Written Opinion for International Application No. PCT/US2014/018347, dated Apr. 17, 2014, 9 pages.
International Search Report and Written Opinion for International Application No. PCT/US2015/044173, dated Oct. 12, 2015, 9 pages.
International Search Report and Written Opinion for International Application No. PCT/US2015/044177, dated Oct. 30, 2015, 10 pages.
International Search Report and Written Opinion for International Application No. PCT/US2015/044183, dated Nov. 4, 2015, 9 pages.
International Search Report and Written Opinion for International Application No. PCT/US2015/044610, dated Nov. 5, 2015, 12 pages.
International Search Report for International Application No. PCT/US2009/069388, dated Jun. 30, 2010.
Written Opinion for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., The "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com [date of publication unknown], pp. 1-16.
Extended European Search Report for European Application No. 17209149.8, dated May 7, 2018, 6 pages.
Office Action for Indian Application No. 333/DELNP/2012, dated Sep. 27, 2018, 6 pages.
Office Action for U.S. Appl. No. 15/675,093, dated Jun. 14, 2019, 12 pages.

* cited by examiner

TRIGGER ASSEMBLY FOR TYMPANOSTOMY TUBE DELIVERY DEVICE

CROSS-REFERENCE TO RELATED APPLICATIONS

This application is a continuation of International Application No. PCT/US2015/044179, entitled "Trigger Assembly for Tympanostomy Tube Delivery Device," filed Aug. 7, 2015, which is a continuation of U.S. patent application Ser. No. 14/457,412, entitled "Trigger Assembly for Tympanostomy Tube Delivery Device," filed Aug. 12, 2014, now U.S. Pat. No. 9,539,146, which is a continuation-in-part of U.S. patent application Ser. No. 12/836,654, entitled "Tympanic Membrane Pressure Equalization Tube Delivery System," filed Jul. 15, 2010, now U.S. Pat. No. 8,864,774, which claims priority to U.S. Provisional Application No. 61/225,893, filed Jul. 15, 2009, the disclosure of each of which is hereby incorporated by reference in its entirety.

BACKGROUND

Some children may exhibit recurrent episodes of otitis media and/or -otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012; and U.S. Pub. No. 2011/0015645, entitled "Tympanic Membrane Pressure Equalization Tube Delivery System," published Jan. 20, 2011, the disclosure of which is incorporated by reference herein. Still additional exemplary pressure equalization tube delivery systems are disclosed in U.S. patent application Ser. No. 13/804,553, entitled "Features to Improve and Sense Tympanic Membrane Apposition by Tympanostomy Tube Delivery Instrument," filed Mar. 14, 2013, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
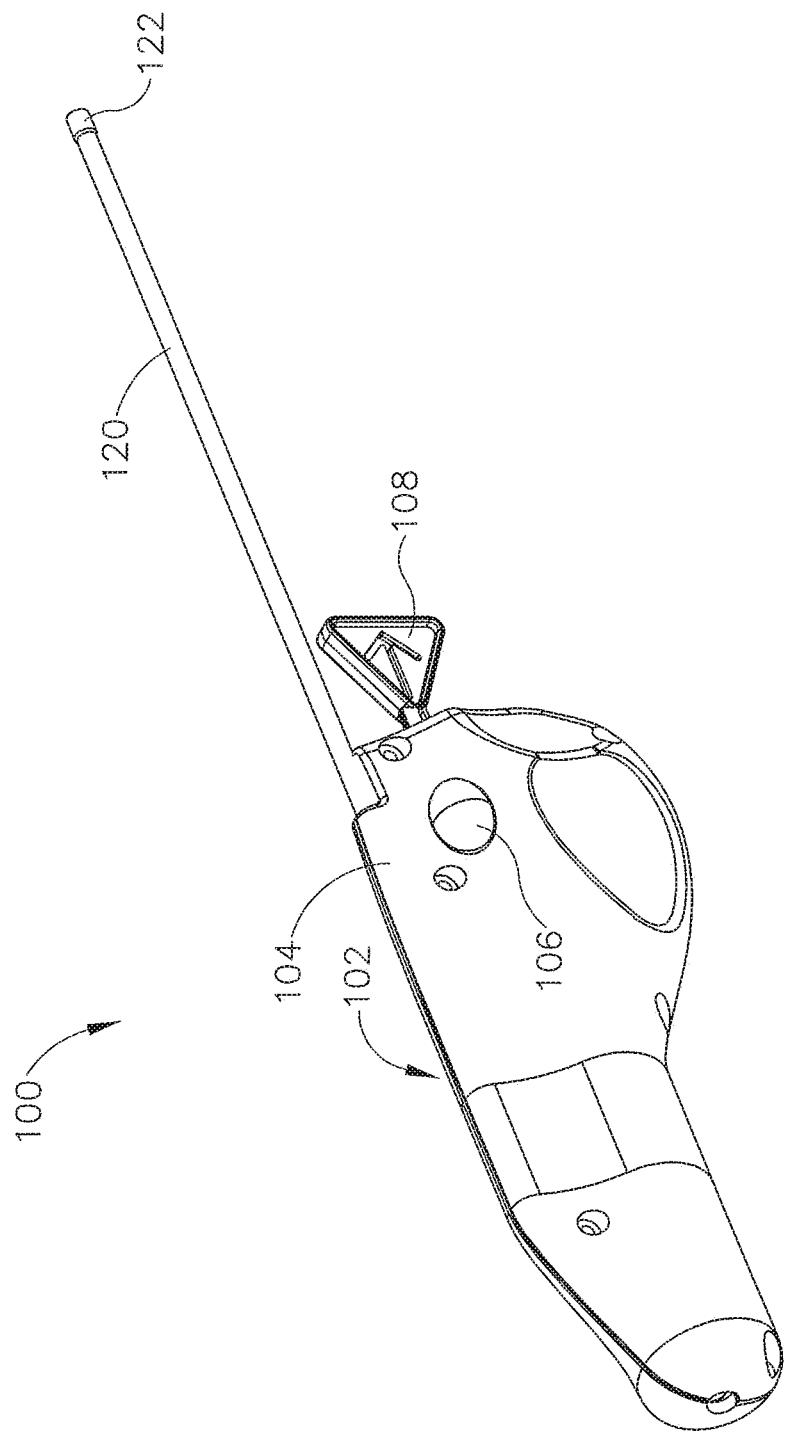
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a handpiece (102) and a cannula (120) extending distally from handpiece (102). Hanpdiece (102) is formed by two housing (104) halves that are joined together and that include internal features configured to support various components of PETDD (100) as will be described below. Handpiece (102) is configured to be handheld, such that an operator may fully operate PETDD (100) using a single hand. A pushbutton (106) is slidably disposed in housing (104) and includes exposed portions extending laterally from each side of handpiece. Pushbutton (106) is operable to be pushed along a path that is transverse to handpiece (102) in order to actuate PETDD (100) as will be described in greater detail below. A pull-pin (108) extends distally from handpiece (102) and is configured to prevent pushbutton (106) from being actuated, thereby preventing PETDD (100) from being actuated, so long as pull-pin (108) is disposed in handpiece (102). Pull-pin (108) is nevertheless removable from handpiece (102) to effectively unlock pushbutton (106) and thereby enable actuation of PETDD (100). Cannula (120) of the present example comprises an elongate tube having a clear tip member (122) at the distal end of cannula (120). Clear tip member (122) is configured to contact a patient's tympanic membrane (TM) while enabling visualization of the distal end of cannula (120). In some versions, tip member (122) is formed of a soft or elastomeric material such as rubber, soft plastic, etc. This may dampen vibrations that might otherwise be transmitted from cannula (120) to the patient's tympanic membrane (TM) during firing of PETDD (100). In addition or in the alternative, tip member (122) may include some other kind of dampening feature as will be apparent to those of ordinary skill in the art in view of the teachings herein.

Figure 2:
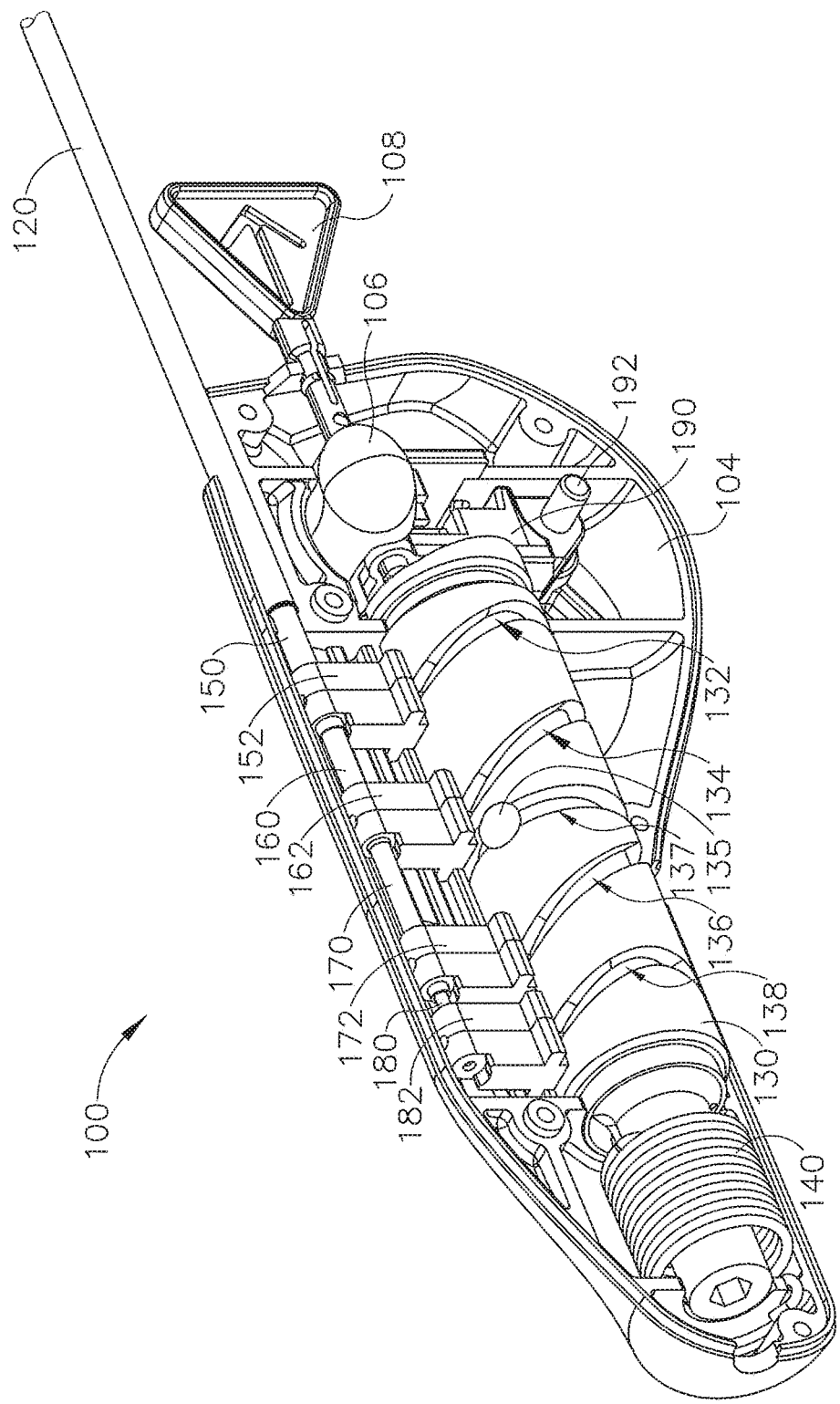
FIG. 2 depicts a perspective view of the PETDD of FIG. 1, with a housing half omitted.

As can be seen in FIG. 2, housing (104) supports a camshaft (130) and various other components. Camshaft (130) includes a dilator track (132), a shield tube track (134), a stopper track (137), a pusher track (136), and a piercer track (138). Tracks (132, 134, 136, 137, 138) are formed as recesses in camshaft (130) and each track (132, 134, 136, 137, 138) has a unique configuration in order to provide a particular sequence of operation of translating components as will be described in greater detail below. A torsion spring (140) is coupled to the proximal end of camshaft (130). Torsion spring (140) is also grounded against housing (104). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), a trigger mechanism selectively resists such rotation. While torsion spring (140) is used to bias camshaft (130) in the present example, it should be understood that any other suitable types of components may be used to bias camshaft (130).

Figure 3:
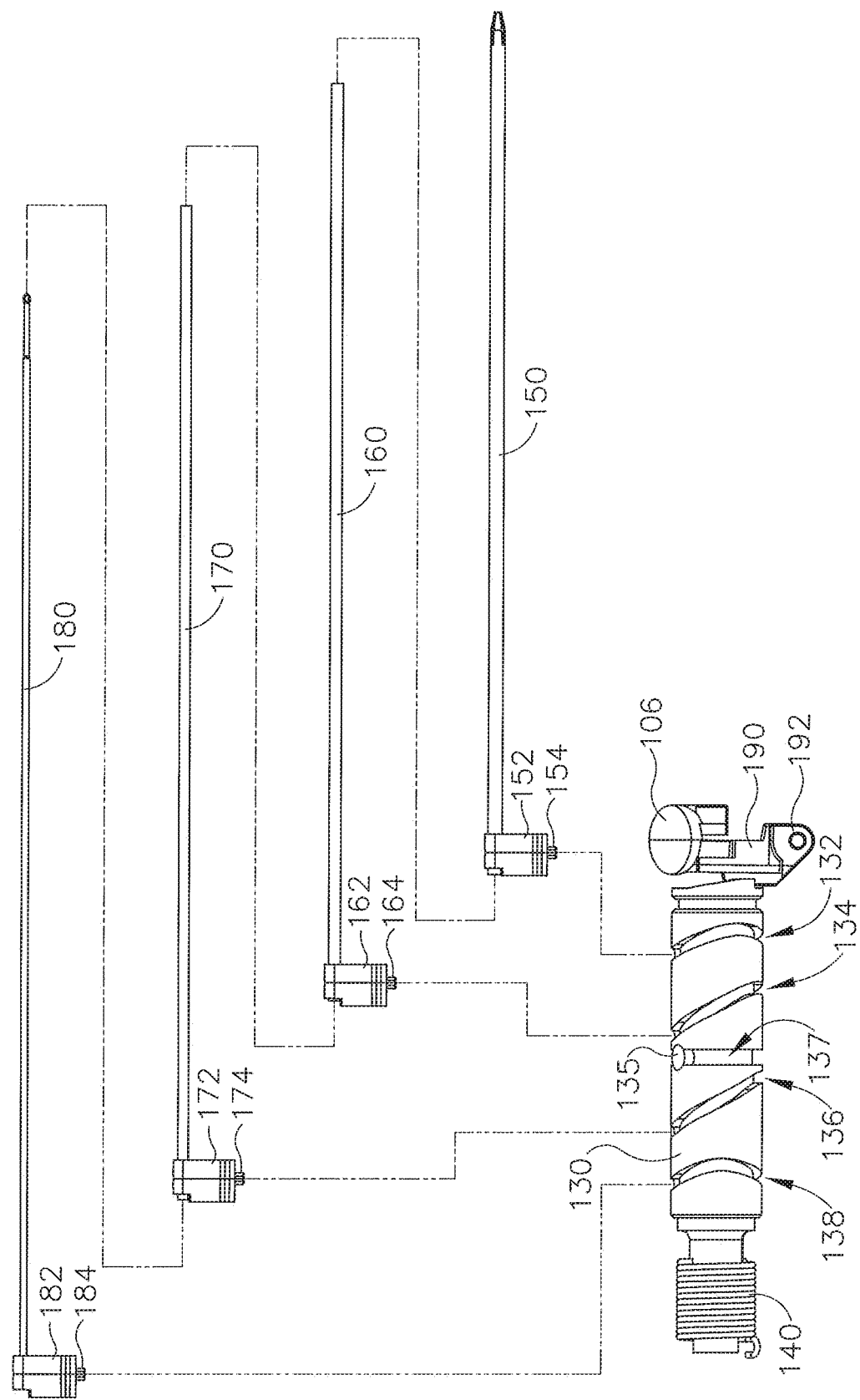
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120). Piercer (180) is coaxially and slidably disposed within pusher tube (170), which is coaxially and slidably disposed within shield tube (160), which is coaxially and slidably disposed within dilator tube (150), which is coaxially and slidably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate. Stopper track (137) is simply annular in this example and includes a fixed elastomeric plug (135). An inwardly protruding boss (not shown) of housing (104) is disposed in stopper track (137). This boss remains disposed in stopper track (137) during rotation of camshaft (130).

Figure 4:
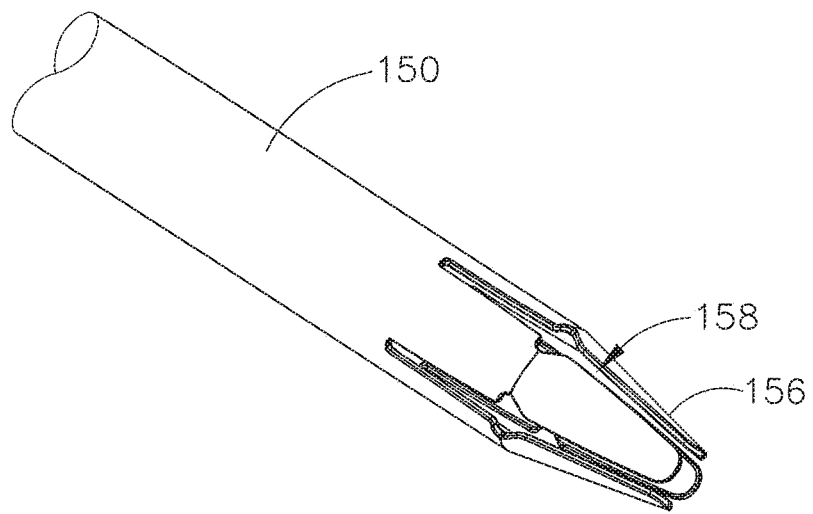
FIG. 4 depicts a perspective view of the distal end of a dilator of the actuation features of FIG. 3.
Figure 5:
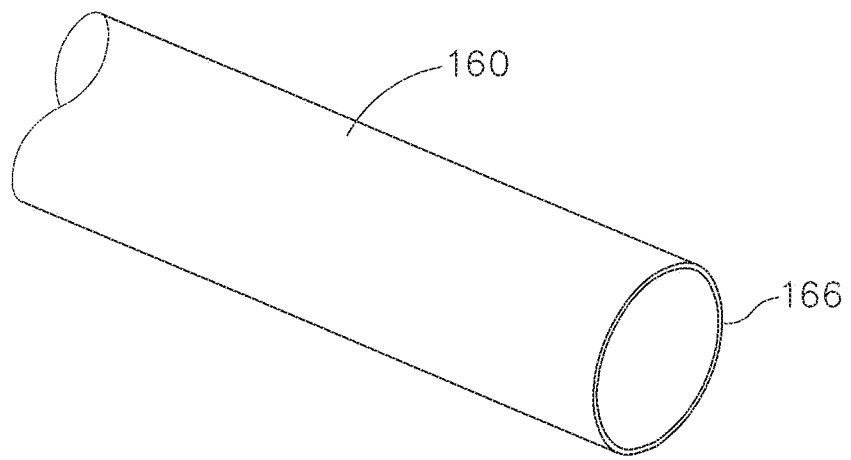
FIG. 5 depicts a perspective view of the distal end of a shield tube of the actuation features of FIG. 3.
Figure 6:
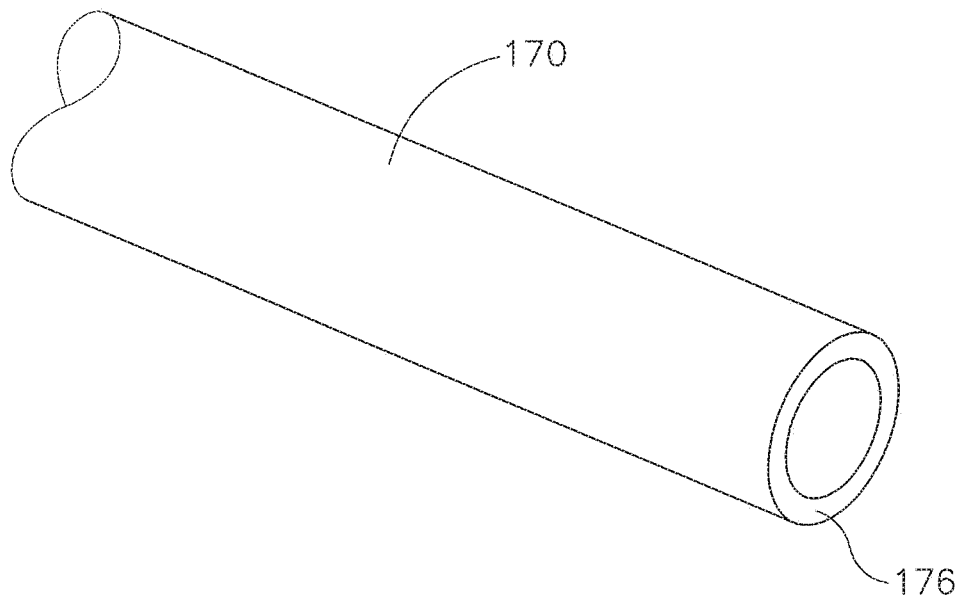
FIG. 6 depicts a perspective view of the distal end of a pusher of the actuation features of FIG. 3.
Figure 7:
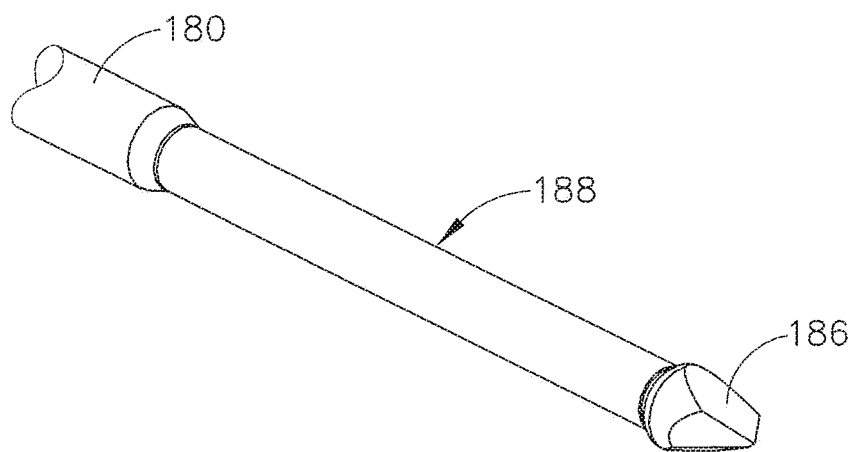
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted piercer tip (186) that is configured to pierce through a patient's tympanic membrane (TM). In the present example, piercer (180) also includes a neck-down region (188) having a reduced diameter.

Figure 8:
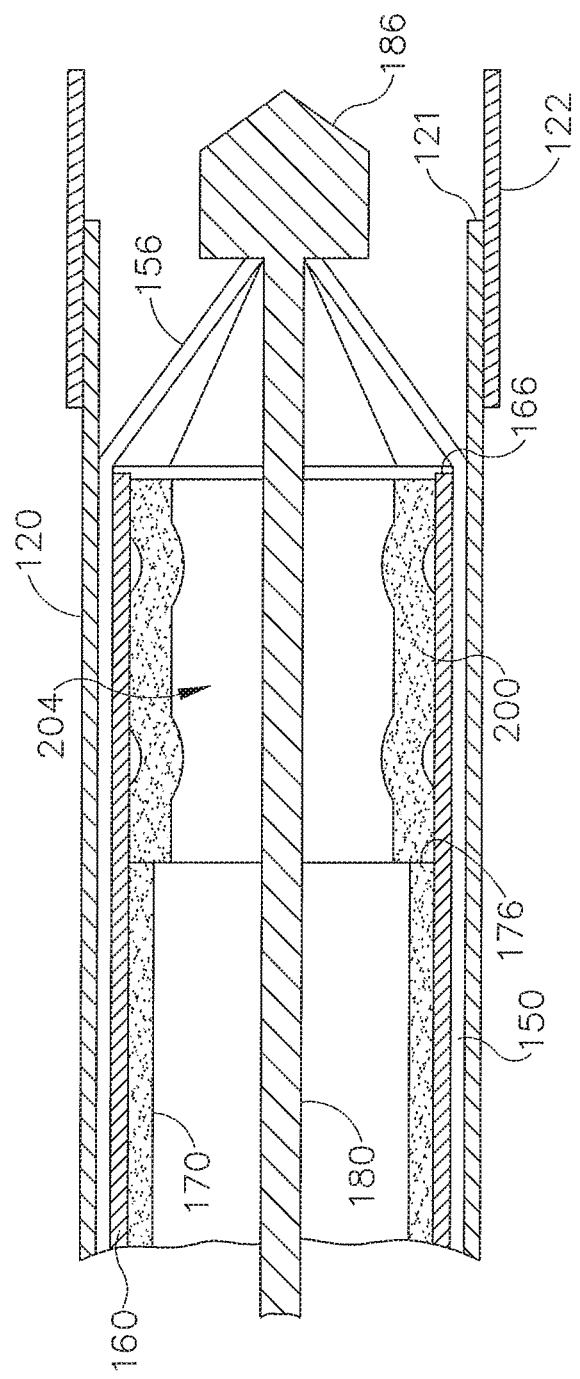
FIG. 8 depicts a cross-sectional side view of the actuation features of FIG. 3 with an exemplary pressure equalization (PE) tube.

FIG. 8 shows the positioning of tubes (150, 160, 170), piercer (180), and PE tube (200) within cannula (120) before camshaft (130) starts rotating from a home position. As shown, piercer tip (186) of piercer (180) is positioned distal to leaves (156) of dilator tube (150), such that leaves (156) are positioned about neck-down region (188) of piercer (180). PE tube (200) is positioned within the distal end of shield tube (160), whose distal edge (166) is just proximal to leaves (156). Pusher tube (170) is proximal to PE tube (200), with distal face (176) of pusher tube (170) abutting the proximal end of PE tube (200). In the present example, PE tube (200) is resiliently biased to assume a rivet-like shape presenting transverse petals (208) and a flange (206) (see FIG. 9). However, PE tube (200) is compressed against this bias, thereby assuming a generally cylindraceous configuration, when PE tube (200) is disposed within shield tube (160) as shown in FIG. 8.

Figure 9:
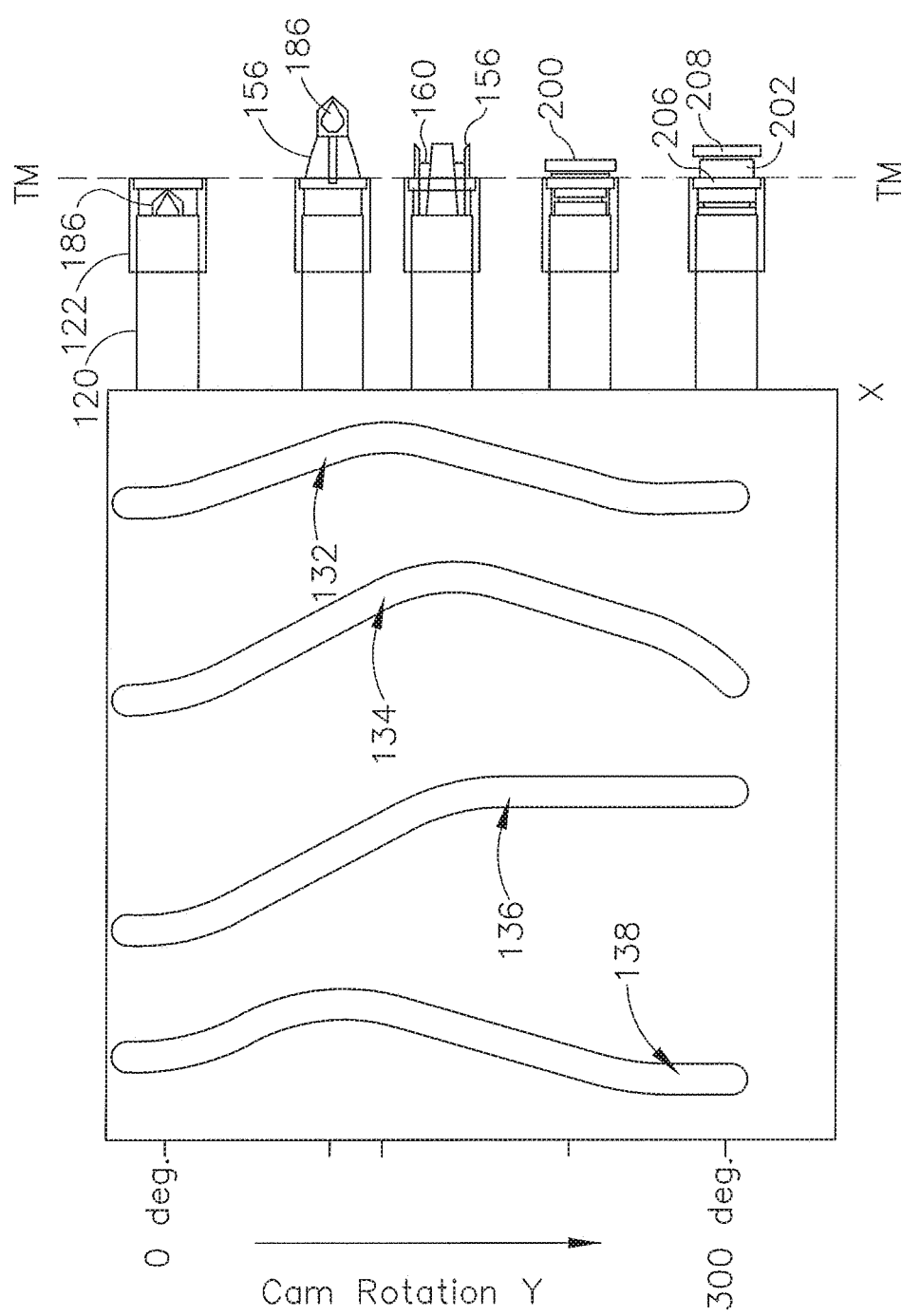
FIG. 9 depicts a displacement and operational diagram associated with the actuation features of FIG. 3.
Figure 10:
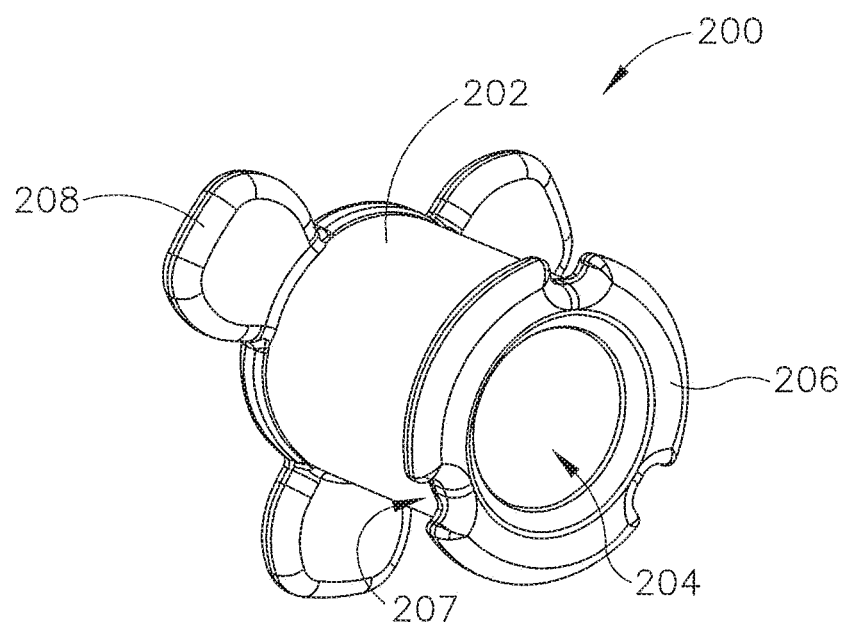
FIG. 10 depicts a perspective view of the proximal side of an exemplary PE tube suitable for delivery by the PETDD of FIG. 1.
Figure 11:
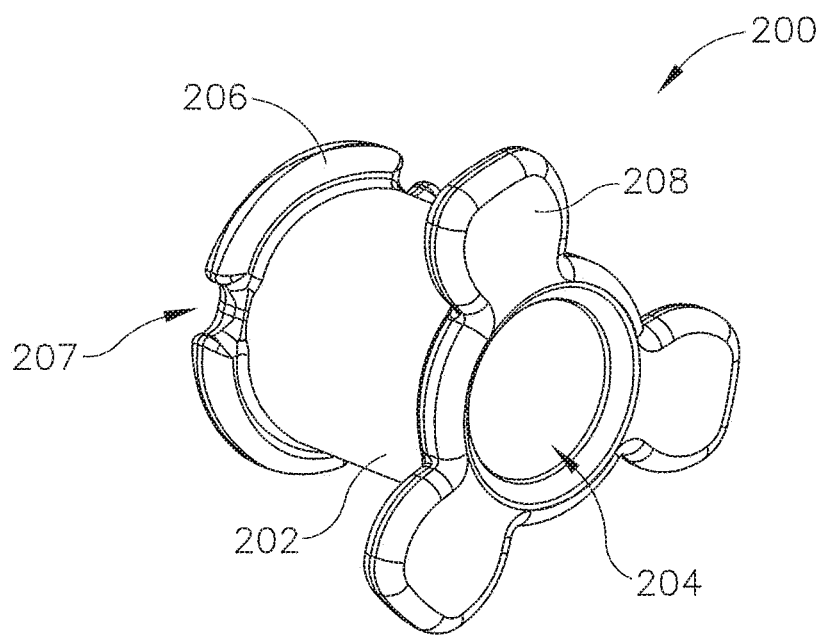
FIG. 11 depicts a perspective view of the distal side of the PE tube of FIG. 10.
Figure 12:
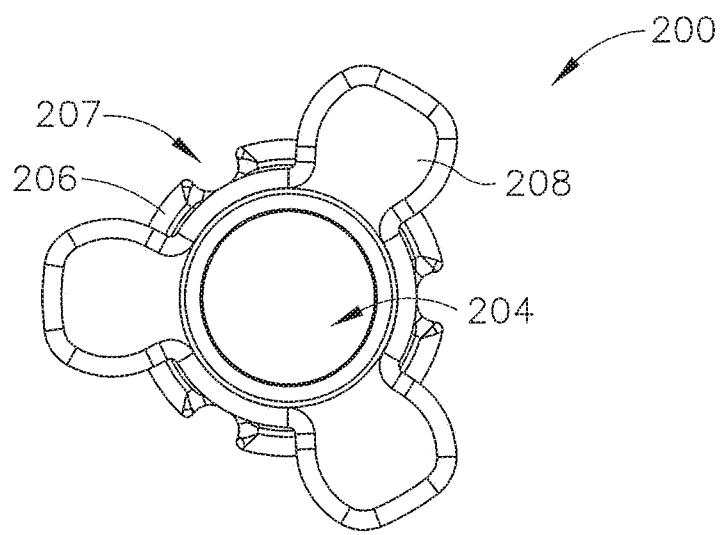
FIG. 12 depicts a distal elevational view of the PE tube of FIG. 10.
Figure 13:
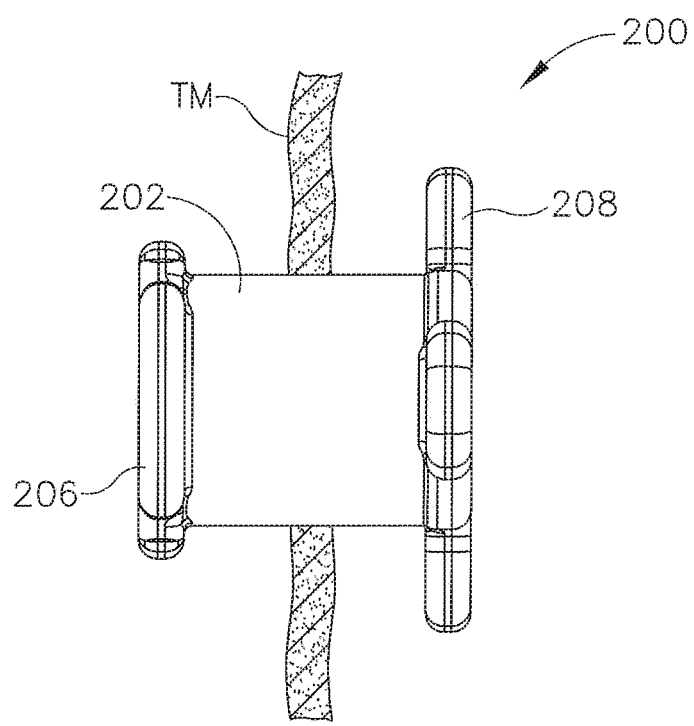
FIG. 13 depicts a side elevational view of the PE tube of FIG. 10, positioned within a tympanic membrane.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip member (122) contacting the patient's tympanic membrane (TM). At this stage, tubes (150, 160, 170), piercer (180), and PE tube (200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the patient's tympanic membrane (TM). While not directly shown in FIG. 8, it should be understood that tubes (160, 170, 190) are also driven distally during this transition, though tubes (160, 170, 190) remain proximal to clear tip member (122) at this stage. As camshaft (130) continues to rotate, piercer (180) begins retracting proximally while tubes (160, 170, 190) continue to advance distally. As shown, shield tube (160) spreads leaves (156) outwardly from their default positions. This further dilates the puncture site in the tympanic membrane (TM). Shield tube (160) continues to contain PE tube (200) at this stage. As camshaft (130) continues to rotate, piercer (180) and dilator (150) retract proximally behind clear tip member (122). Shield tube (160) also begins to retract proximally, while pusher tube (170) remains longitudinally stationary. This relative movement uncovers the distal end of PE tube (200), such that the resilient bias of petals (208) causes petals (208) to flex to transverse positions, thereby effectively forming a flange on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (200), such that the resilient bias of PE tube (200) is allowed to form flange (206) on the near side of the tympanic membrane (TM).

Camshaft (130) stops rotating when the inwardly protruding boss of housing (104) engages plug (135) in stopper track (137). The elastomeric nature of plug (135) provides a relatively soft stop, such that plug (135) acts as a damper. This may reduce jolting of PETDD (100) when camshaft (130) comes to a stop and/or may prevent camshaft (130) from making a popping or snapping sound when camshaft (130) comes to a stop. Upon completion of the above described sequence shown in FIG. 9, cannula (120) is withdrawn from the patient's ear, leaving the actuated PE tube (200) in place in the patient's tympanic membrane (TM). Petals (208) and flange (206) cooperate to maintain the position of PE tube (200) in TM, while the passageway (204) formed by the interior of PE tube (200) (see FIGS. 8 and 10-13) provides a path for fluid communication (e.g., venting) between the patient's middle ear and outer ear. This fluid path further provides pressure equalization between the patient's middle ear and outer ear and/or promotes drainage of fluid from the middle ear via the Eustachian tube.

It should be understood that the foregoing components, features, and operabilities of PETDD (100) are merely illustrative examples. A PETDD (100) may include various other features in addition to or in lieu of those described above. By way of example only, any of the devices herein may also include one or more of the various features disclosed in any of the various references that are incorporated by reference herein. Some additional merely illustrative variations of PETDD (100) will be described in greater detail below, while other variations of PETDD (100) will be apparent to those of ordinary skill in the art in view of the teachings herein.

II. Exemplary Pressure Equalization Tube

FIGS. 10-13 show PE tube (200) in greater detail. PE tube (200) of this example includes a cylindraceous body (202) that defines a passageway (204). A flange (206) is located at the proximal end of body (202) while a set of petals (208) are located at the distal end of body (202). Flange (206) includes a plurality of inwardly directed recesses (207). Recesses (207) are configured to facilitate flexing of flange (206) from an outwardly extended position to a generally cylindraceous position where the material forming flange (206) extends longitudinally. While three recesses (207) are shown, it should be understood that any other suitable number of recesses (207) may be provided. Similarly, while three petals (208) are shown, it should be understood that any other suitable number of petals (208) may be provided.

PE tube (200) is formed of a resilient material that is biased to assume the rivet like configuration shown in FIGS. 10-13. However, flange (206) and petals (208) may be flexed inwardly toward the longitudinal axis of body (202) to provide PE tube (200) with a cylindraceous configuration. In particular, flange (206) and petals (208) may be flexed such that their outer surfaces are at the same radial distance from the longitudinal axis as the outer perimeter of body (202). This radial distance may be slightly less than the radial distance associated with the inner diameter of shield tube (160), such that PE tube (200) may collapse to fit within shield tube (160). When PE tube (200) is disposed in a tympanic membrane (TM), petals (208) are located medially (i.e., on the middle ear side) while flange (206) is located laterally (i.e., on the outer ear side). By way of example only, PE tube (200) may also be configured in accordance with at least some of the teachings of U.S. patent application Ser. No. 13/800,113, entitled "Tympanic Membrane Pressure Equalization Tube," filed on Mar. 13, 2013, the disclosure of which is incorporated by reference herein. Other suitable forms that PE tube (200) may take will be apparent to those of ordinary skill in the art in view of the teachings herein.

III. Exemplary Pressure Equalization Tube Delivery with Stability and Motion Predictability Features It will be appreciated that external and/or internal forces may interfere with the steadiness and/or predictability of motion of a PETDD during use. Thus, it may be desirable to provide a PETDD with features configured to improve steadiness and predictability of motion during use. For instance, such features may improve steadiness and predictability of motion during activation by the user and/or operation of the components of such a PETDD. A PETDD may also be modified to reduce friction between moving elements that are moved to actuate the PETDD. For instance, a modified version of PETDD (100) may provide a variation of pushbutton (106) that provides less friction to actuate the modified PETDD (100) (e.g., by relying on a pivoting trigger motion instead of a sliding trigger motion). As will be discussed in more detail below, FIGS. 14-26 show such an exemplary alternative PETDD (400) having features configured to improve steadiness and predictability of motion during use; and to reduce friction during the triggering of the actuation of PETDD (400). Various examples of such features will be described in greater detail below; while other examples will be apparent to those of ordinary skill in the art according to the teachings herein. It should be understood that PETDD (400) described below is configured to function substantially similar to PETDD (100) described above except for the differences described below. In particular, PETDD (400) described below may be used to insert a PE tube (200) within the tympanic membrane (TM) of the patient.

A. Exemplary Motion Limiting Features

Figure 14:
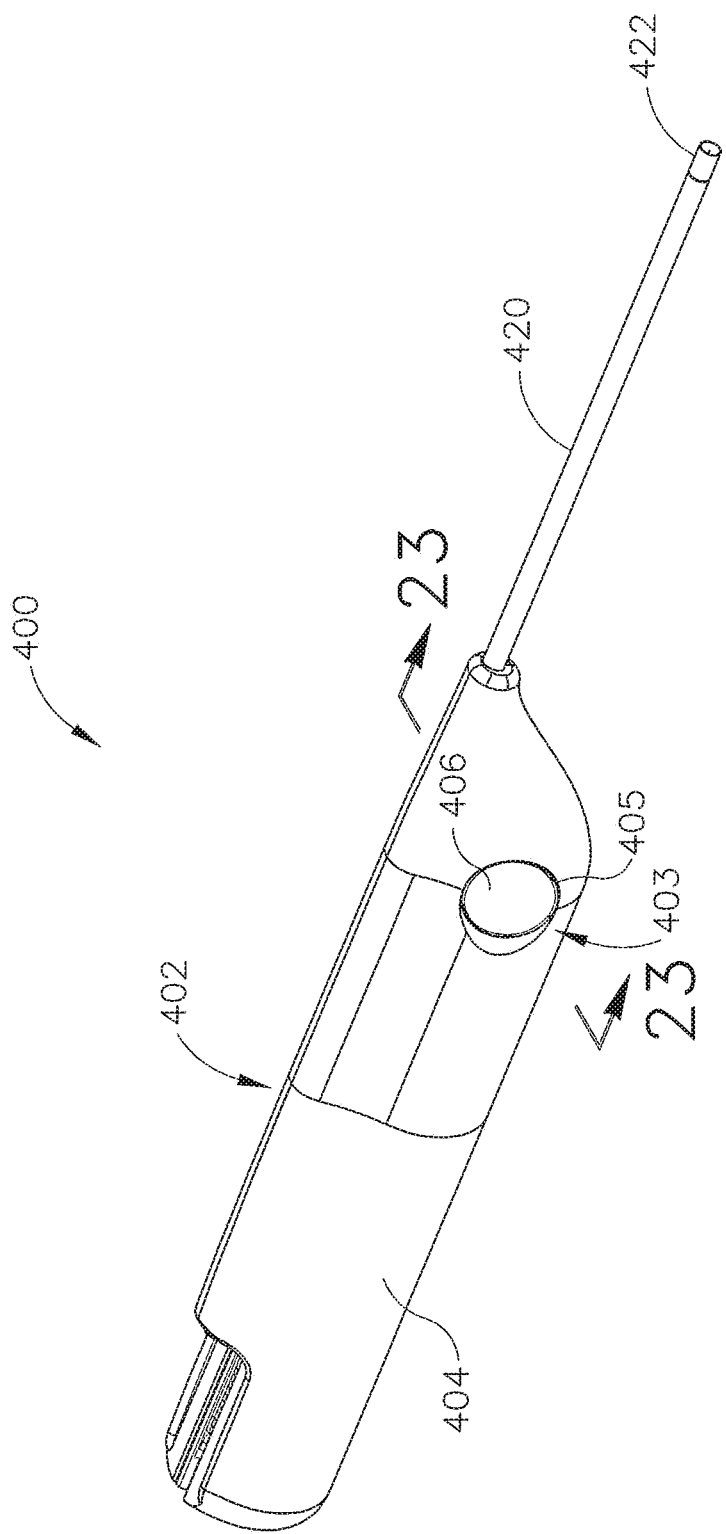
FIG. 14 depicts a perspective view of an exemplary alternative PETDD.
Figure 15:
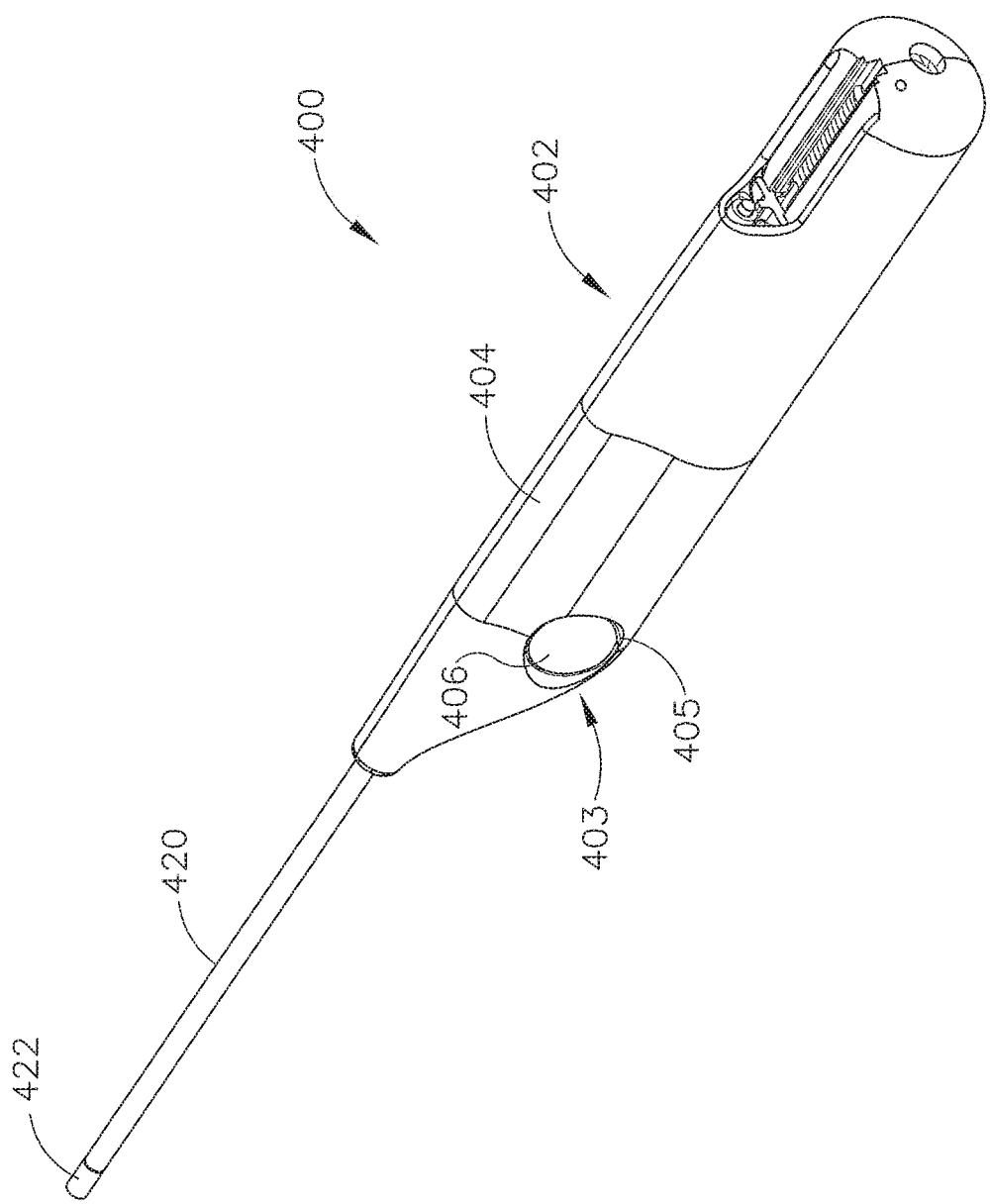
FIG. 15 depicts another perspective view of the PETDD of FIG. 14.

As shown in FIGS. 14 and 15, PETDD (400) of this example comprises a handpiece (402) and a cannula (420) extending distally from handpiece (402). Hanpdiece (402) is formed by two housing (404) halves that are joined together and that include internal features configured to support various components of PETDD (400) as will be described below. Handpiece (402) is configured to be handheld, such that an operator may fully operate PETDD (400) using a single hand. A pushbutton (406) is hingedly coupled within an opening (403) of each housing (404) half via a living hinge (405). Pushbuttons (406) include exposed portions extending laterally from each side of handpiece (402). As will be described in more detail below, each pushbutton (406) is operable to be pivoted about a respective living hinge (405) to actuate PETDD (400). Cannula (420) of the present example comprises an elongate tube having a clear tip member (422) at the distal end of cannula (420). Clear tip member (422) is configured to contact a patient's tympanic membrane (TM) while enabling visualization of the distal end of cannula (420). In some versions, tip member (420) is formed of a soft or elastomeric material such as rubber, soft plastic, etc. This may dampen vibrations that might otherwise be transmitted from cannula (420) to the patient's tympanic membrane (TM) during firing of PETDD (400). In addition or in the alternative, tip member (422) may include some other kind of dampening feature as will be apparent to those of ordinary skill in the art in view of the teachings herein; or tip member (422) may be omitted altogether.

Figure 16:
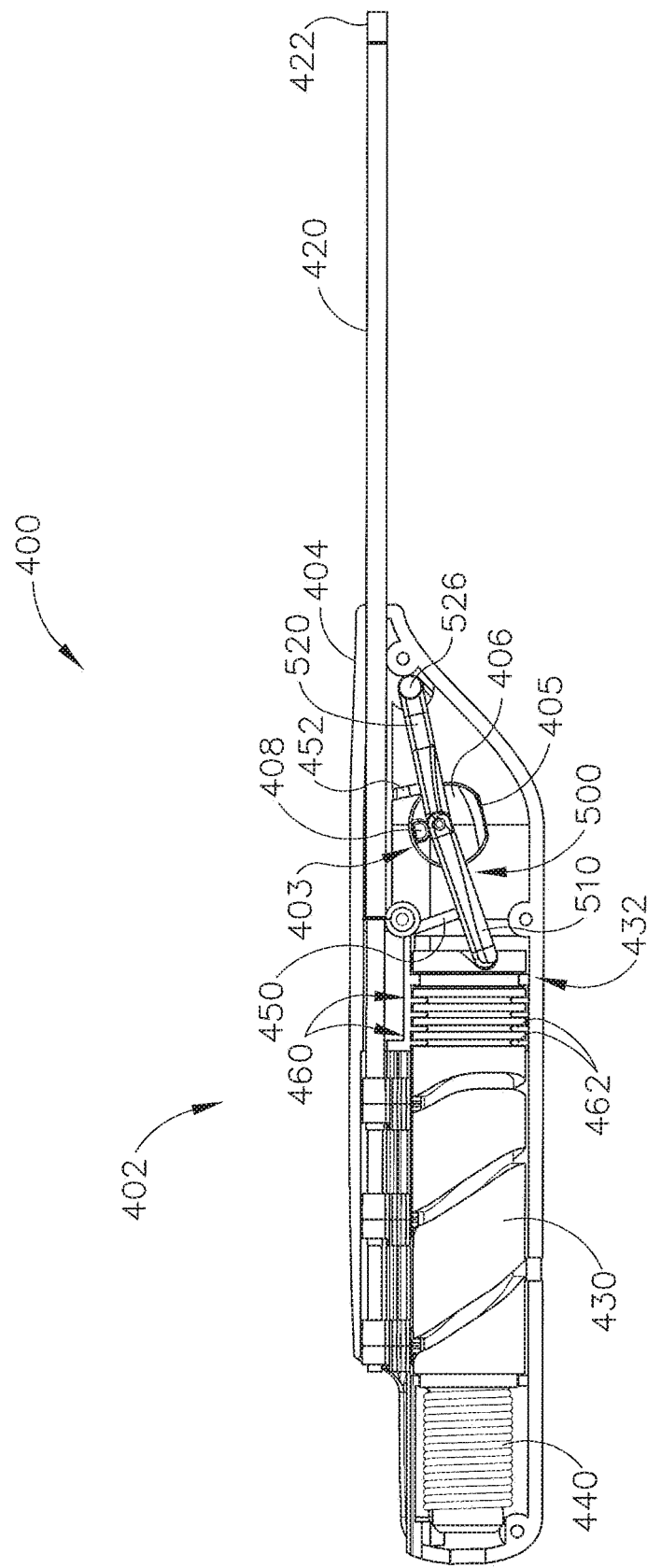
FIG. 16 depicts a side elevational view of the PETDD of FIG. 14, with a housing half omitted.
Figure 17:
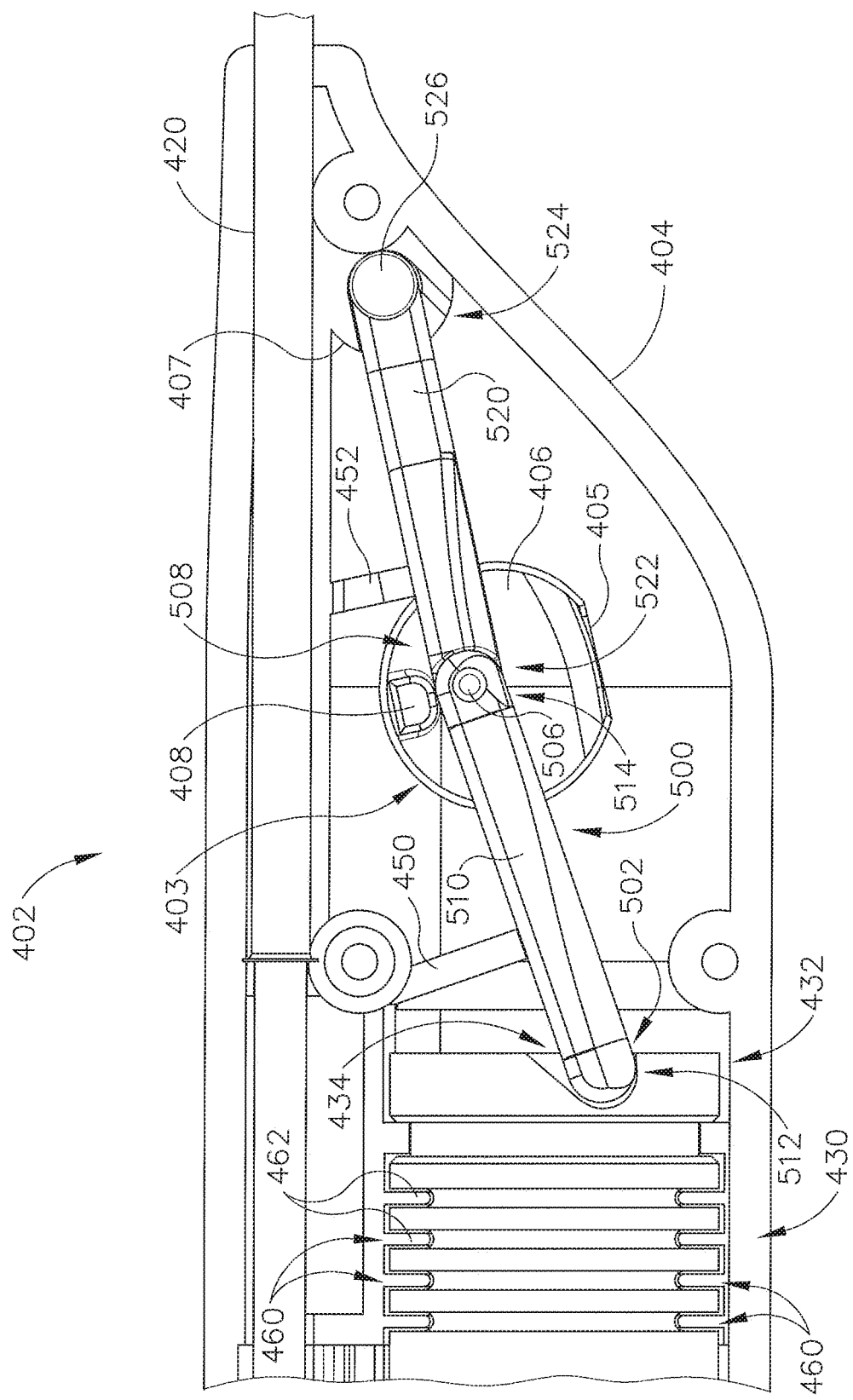
FIG. 17 depicts a side elevational view of a distal portion of the PETDD of FIG. 14, with a housing half omitted.
Figure 18:
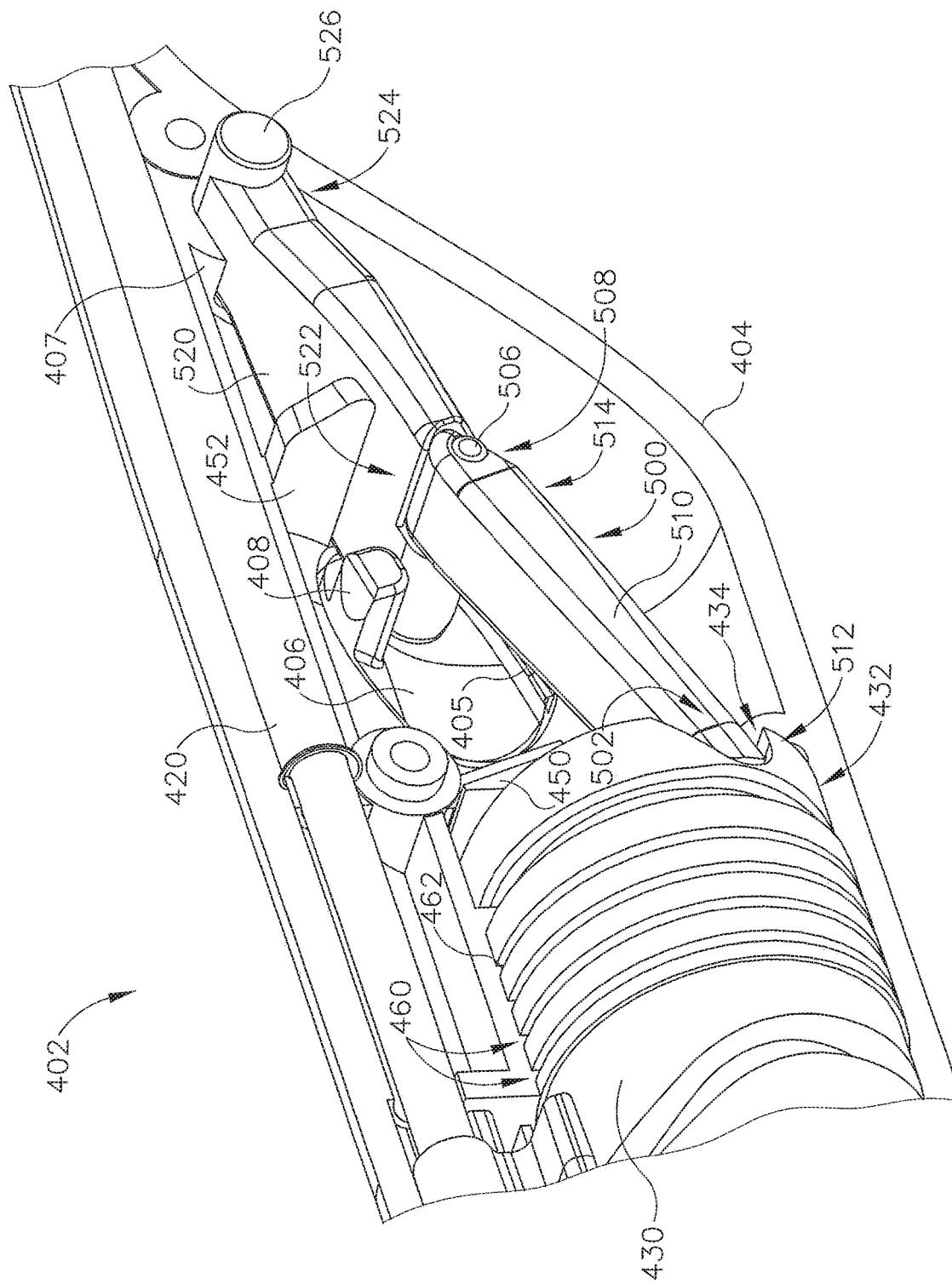
FIG. 18 depicts a perspective view of the distal portion of the PETDD of FIG. 14, with a housing half omitted.
Figure 19:
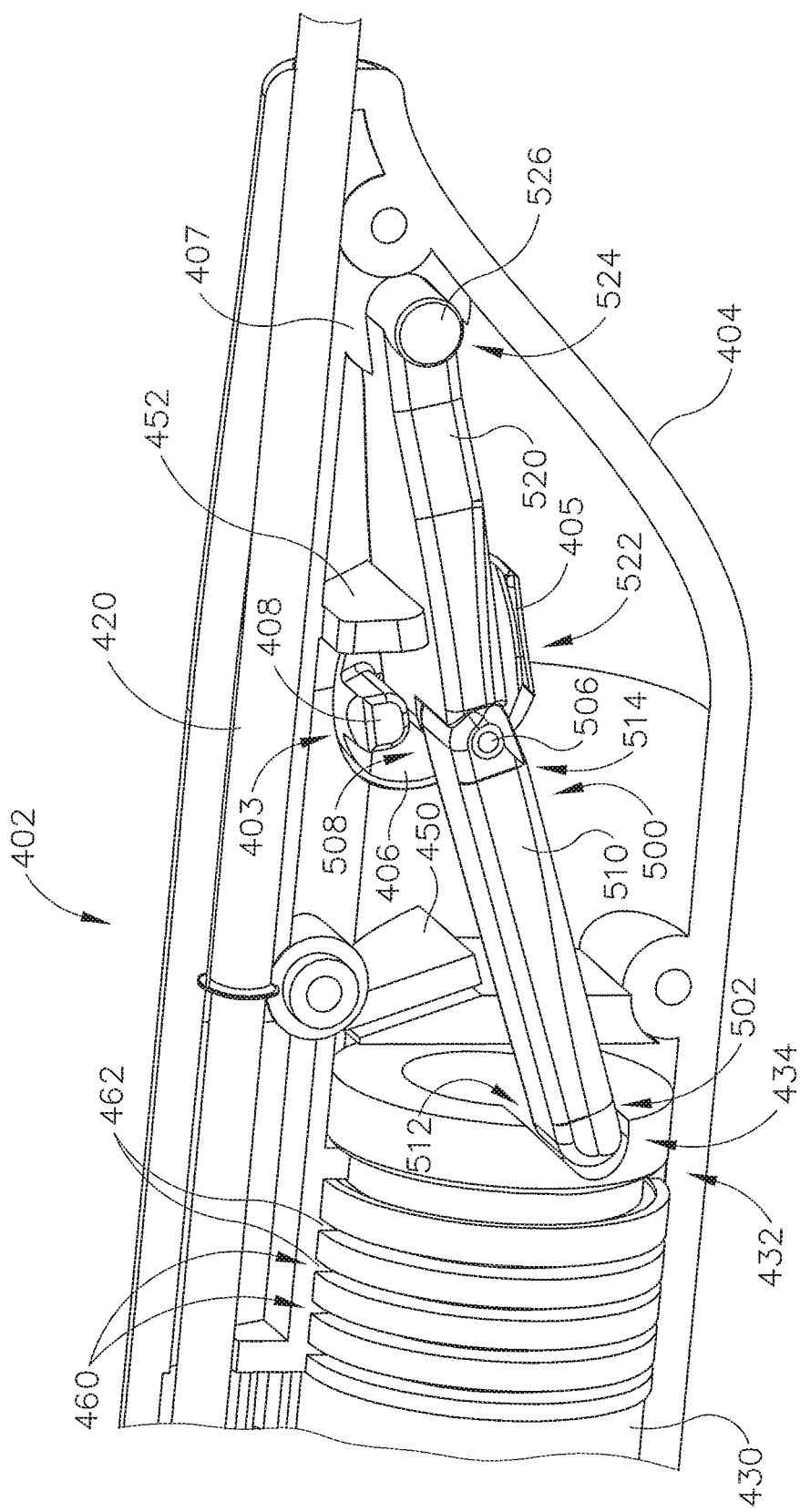
FIG. 19 depicts another perspective view of the distal portion of the PETDD of FIG. 14, with a housing half omitted.
Figure 20:
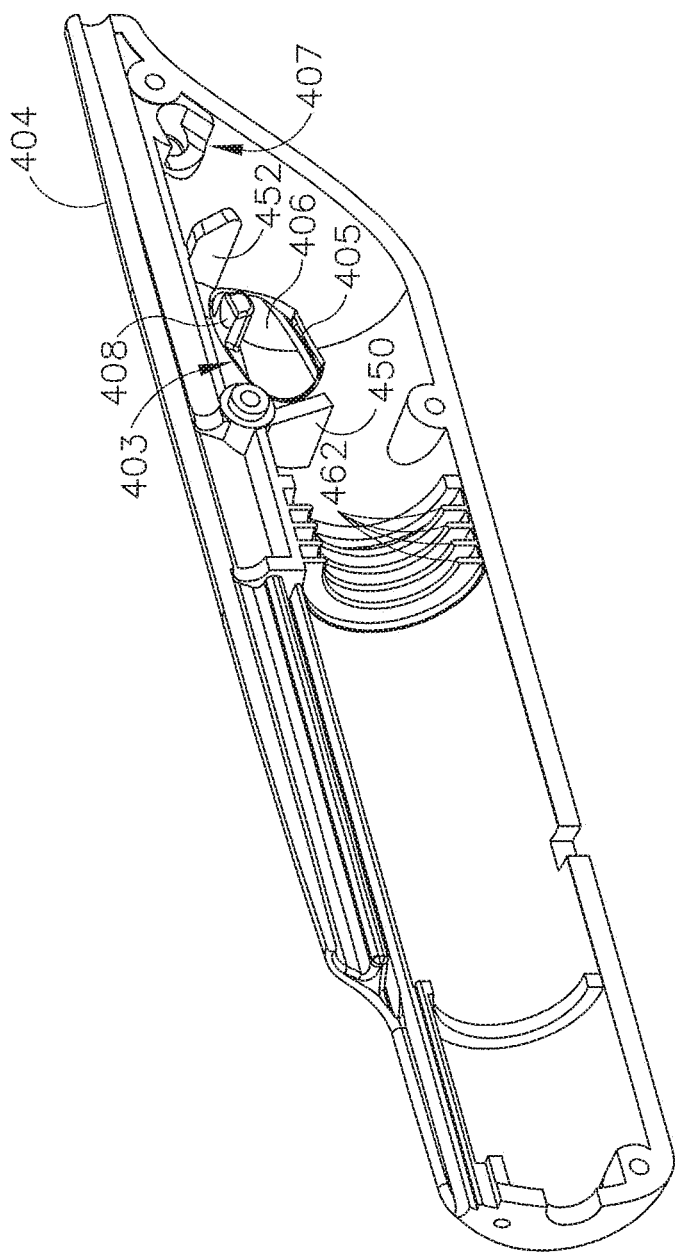
FIG. 20 depicts a perspective view of a housing half of the PETDD of FIG. 14.
Figure 21:
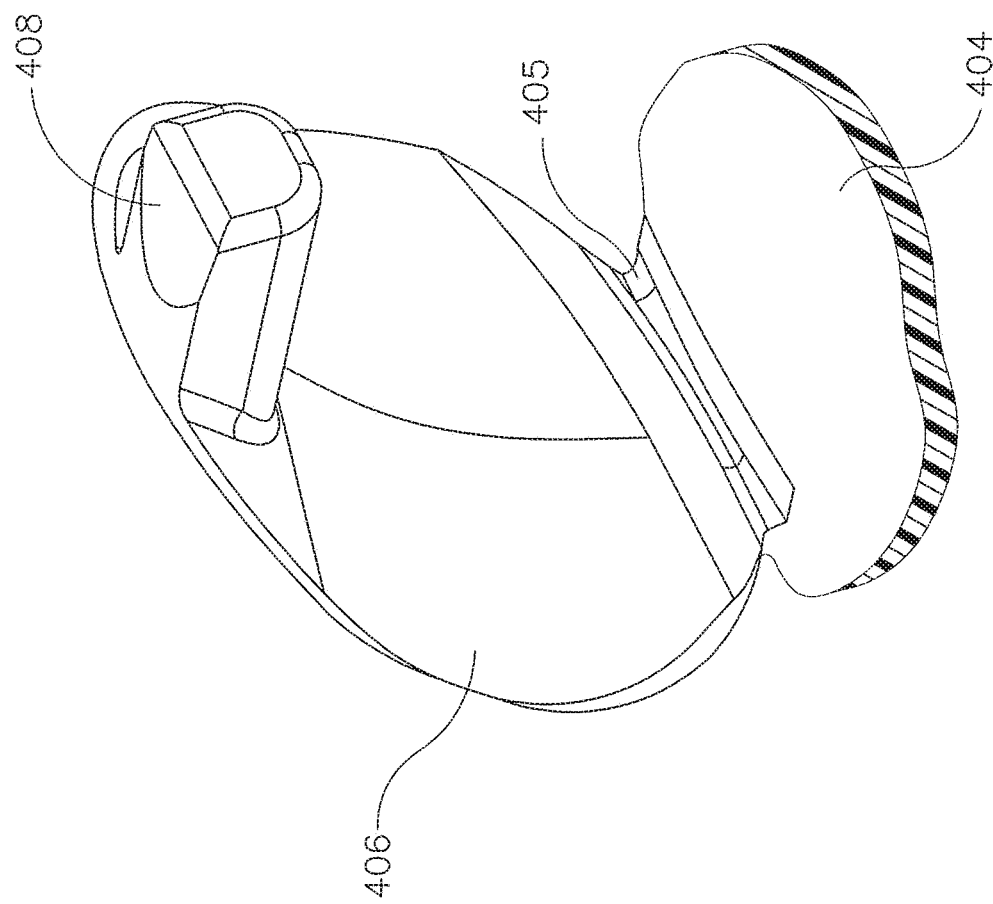
FIG. 21 depicts a perspective view of an integral button of the PETDD of FIG. 14.

As can be seen in FIG. 16, housing (404) supports a camshaft (430) and various other components. Camshaft (430) is configured to operate substantially similar to camshaft (130) discussed above except for the differences discussed below. For instance, camshaft (430) is configured to rotate to thereby provide a particular sequence of operation of translating components as was discussed above with reference to PETDD (100). A torsion spring (440) is coupled to the proximal end of camshaft (430). Torsion spring (440) is also grounded against housing (404). Torsion spring (440) resiliently provides a rotational bias to camshaft (430). In particular, torsion spring (440) urges camshaft (430) to rotate in the clockwise direction (viewed from the distal end of PETDD (400) toward the proximal end of PETDD (400)) about the longitudinal axis of camshaft (430). As will be described in greater detail below, a collapsible linkage (500) selectively resists such rotation. In particular, and as best seen in FIGS. 17-19, a distal end (432) of camshaft (430) comprises a notch (434). Notch (434) is configured to receive a proximal end (502) of collapsible linkage (500) to thereby prevent clockwise rotation of camshaft (430). While torsion spring (440) is used to bias camshaft (430) in the present example, it should be understood that any other suitable types of components may be used to bias camshaft (430).

Figure 23:
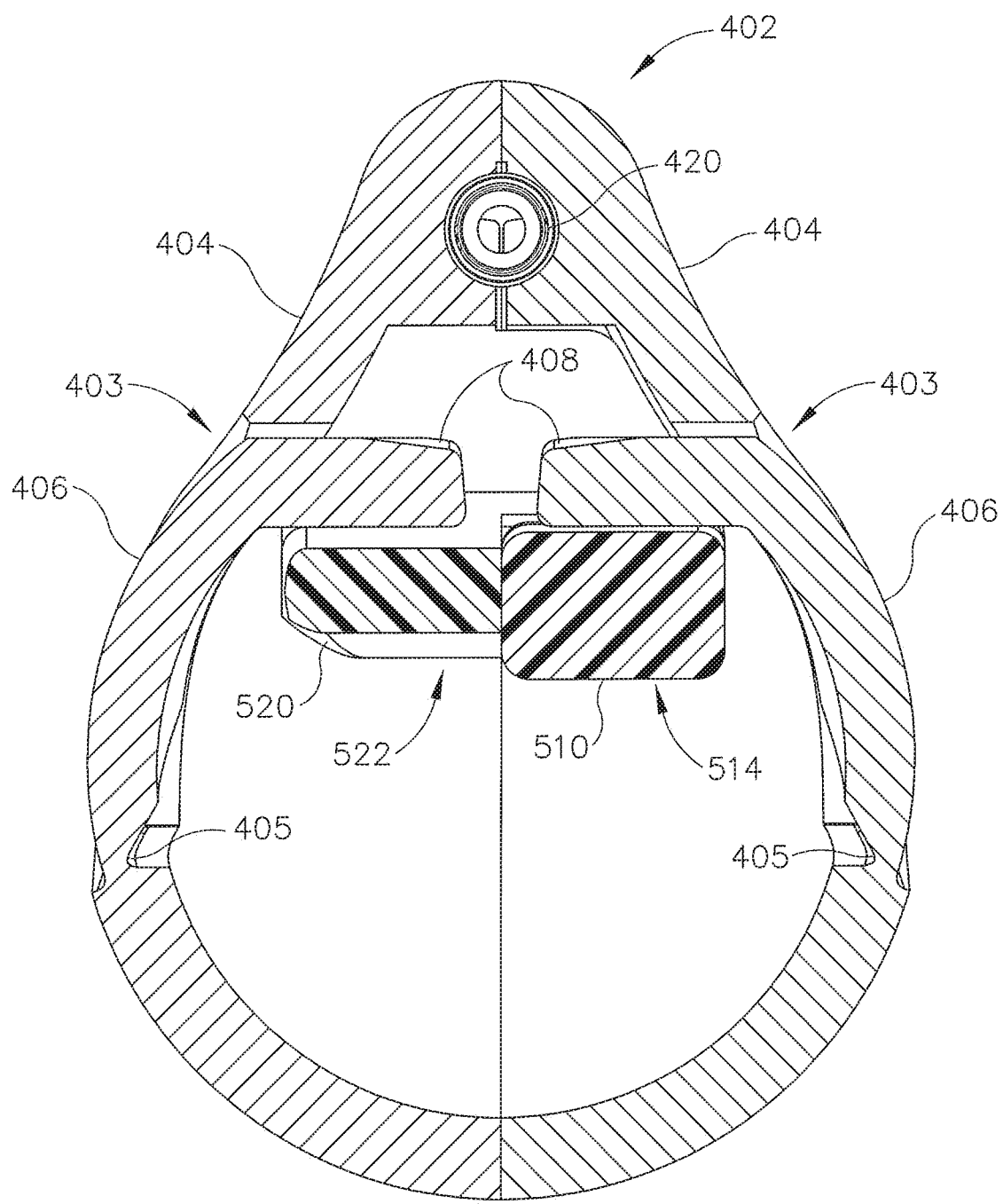
FIG. 23 depicts a cross-sectional rear view of the PETDD of FIG. 14, taken along line 23-23 of FIG. 14.

As mentioned above, and as best seen in FIGS. 20 and 21, pushbutton (406) is rotatably disposed within opening (403) of housing (404). As best seen in FIG. 23, PETDD (400) of the present example comprises two pushbuttons (406) disposed on opposite sides of handpiece (402). Pushbutton (406) is hingedly coupled to housing (404) within opening (403) via living hinge (405) such that pushbutton (406) may be pivoted about living hinge (405) relative to opening (403). Pushbutton (406) is resiliently biased toward a "home" position as shown FIG. 20. In the "home" position, a portion of pushbutton (406) is exposed and extends laterally from the corresponding side of handpiece (402). A user may engage pushbutton (406) in the "home" position to thereby pivot pushbutton (406) inwardly relative to housing (404) about living hinge (405). Pushbutton (406) comprises an integral, inwardly extending post (408). As will be described in more detail below, pushbutton (406) is operable to be pivoted about living hinge (405) to thereby cause post (408) to engage collapsible linkage (500) so as to actuate PETDD (400). In some versions of PETDD (400), each half of housing (404) comprises molded plastic, with living hinge (405), pushbutton (406), and post (408) being formed as integral, molded features of housing (404). In some other versions of PETDD (400), pushbutton (406) and post (408) are formed separately and are secured to housing (404) via a hinge that operates similar to living hinge (405). For instance, a separately formed pushbutton (406) may be pivotally joined to a half of housing (404) via a pin (not shown).

Figure 22:
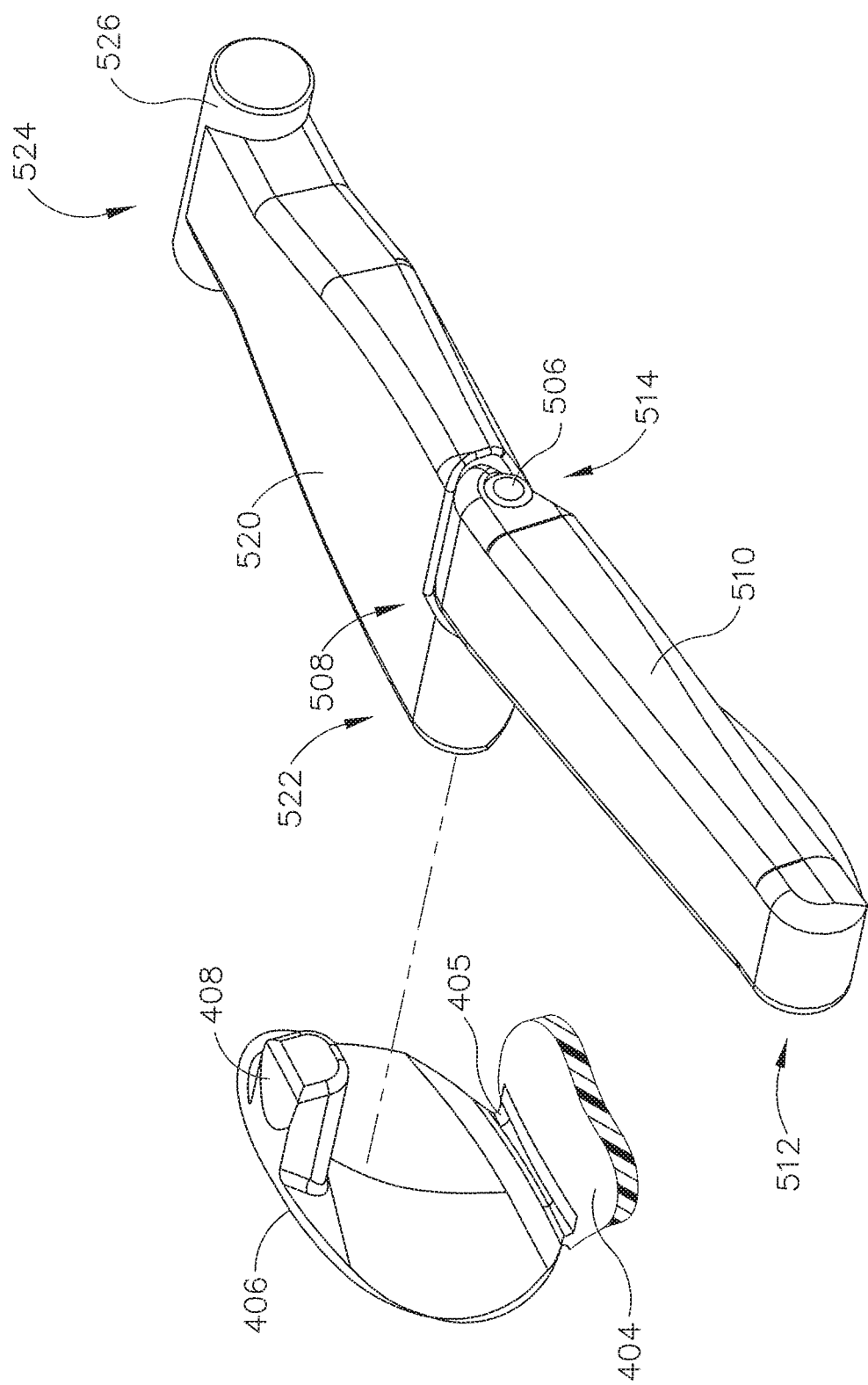
FIG. 22 depicts an exploded perspective view of the integral button of FIG. 21 and a collapsible link of the PETDD of FIG. 14.

As best seen in FIG. 22, collapsible linkage (500) comprises a first link (510) and a second link (520). A distal end (514) of first link (510) is rotatably coupled to a proximal end (522) of second link (520) via a pin (506) such that first link (510) and second link (520) are pivotable about pin (506) relative to one another. (Hereinafter, the portion of collapsible linkage (500) including the distal end (514) of first link (510), the proximal end (522) of second link (520), and pin (506) will be collectively referred to as "linkage portion (508)" of collapsible linkage (500).) A distal end (524) of second link (520) comprises a cylindrical projection (526). Second link (520) is rotatably coupled to an interior boss feature (407) of housing (404) via cylindrical projection (526) such that second link (520) and first link (510) (i.e. collapsible linkage (500)) are rotatable about cylindrical projection (526) within handpiece (402). As will be discussed in more detail below, a proximal end (512) of first link (510) is configured to be positioned within notch (434) of camshaft (430) to thereby prevent clockwise rotation of camshaft (430). Proximal end (512) of first link (510) thus acts as a pawl, as will be described in greater detail below. Also as will be described in more detail below, pushbutton (406) is operable to be pivoted inwardly from the "home" position about living hinge (405) to thereby cause post (408) to engage a top surface of linkage portion (508) of collapsible linkage (500) so as to cause collapsible linkage (500) to collapse. Collapsible linkage (500) is configured such that upon collapsing, proximal end (512) of first link (510) disengages from notch (434) of camshaft (430) to thereby actuate PETDD (400). Collapsible linkage (500) thus acts as an over-center toggle assembly, as will be describe in greater detail below.

Figure 24A:
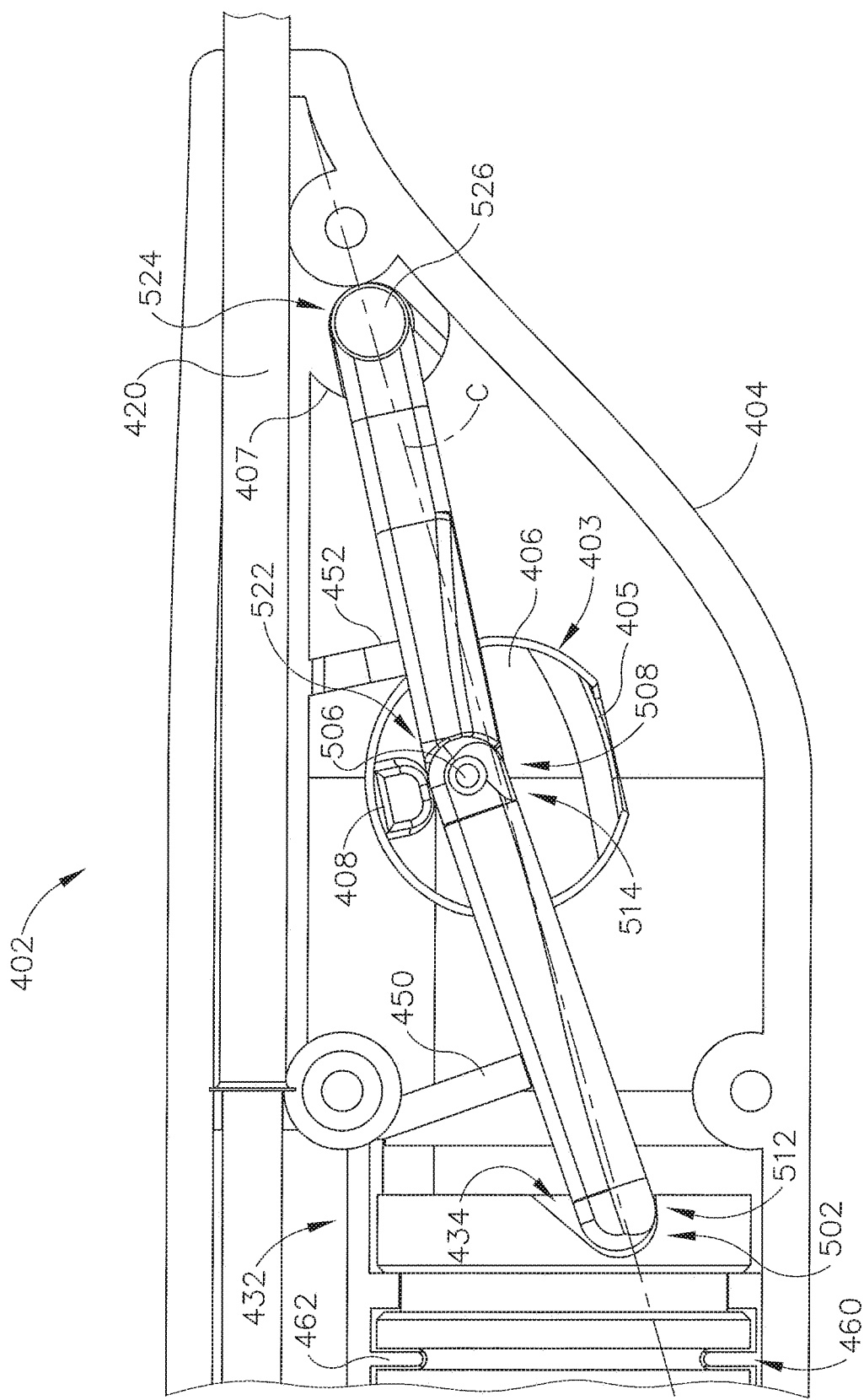
FIG. 24A depicts a side elevational view of the PETDD of FIG. 14 with a housing half omitted, with the integral button of FIG. 21 in a first rotational position, with the collapsible link of FIG. 22 in a first position above a centerline of the collapsible link, and with a rotating cam in a locked position.

FIGS. 24A-25C show the steps of actuation/operation of pushbutton (406), collapsible linkage (500), and generally PETDD (400). As shown in FIGS. 24A and 25A, collapsible linkage (500) is initially in a "static" position. In this "static" position, collapsible linkage (500) is in a bent configuration such that linkage portion (508) of collapsible linkage (500) is above a centerline (C) of collapsible linkage (500). Also in this "static" position, proximal end (512) of first link (510) is positioned within notch (434) of camshaft (430) to thereby resisting rotation of camshaft (430). Because torsion spring (440) resiliently provides a rotational bias to camshaft (430), camshaft (430) imparts an upwardly directed force upon first link (510) via proximal end (512) of first link (510) positioned within notch (434). Collapsible linkage (500) is made substantially rigid and resists this upwardly directed force via a pair of boss supports (450, 452) and cylindrical projection (526) of second link (520). Supports (450, 452) are integrally formed features of housing (404) and extend downwardly from an interior surface of housing (404). Supports (450, 452) engage a top surface of first link (510) and second link (520) of collapsible linkage (500) to thereby restrict upward collapse of collapsible linkage (500). Finally, with collapsible linkage (500) in the "static" position, and with pushbutton (406) in the "home" position, post (408) is at a position above linkage portion (508) of collapsible linkage (500). In particular, post (408) is directly above pin (506).

Figure 24B:
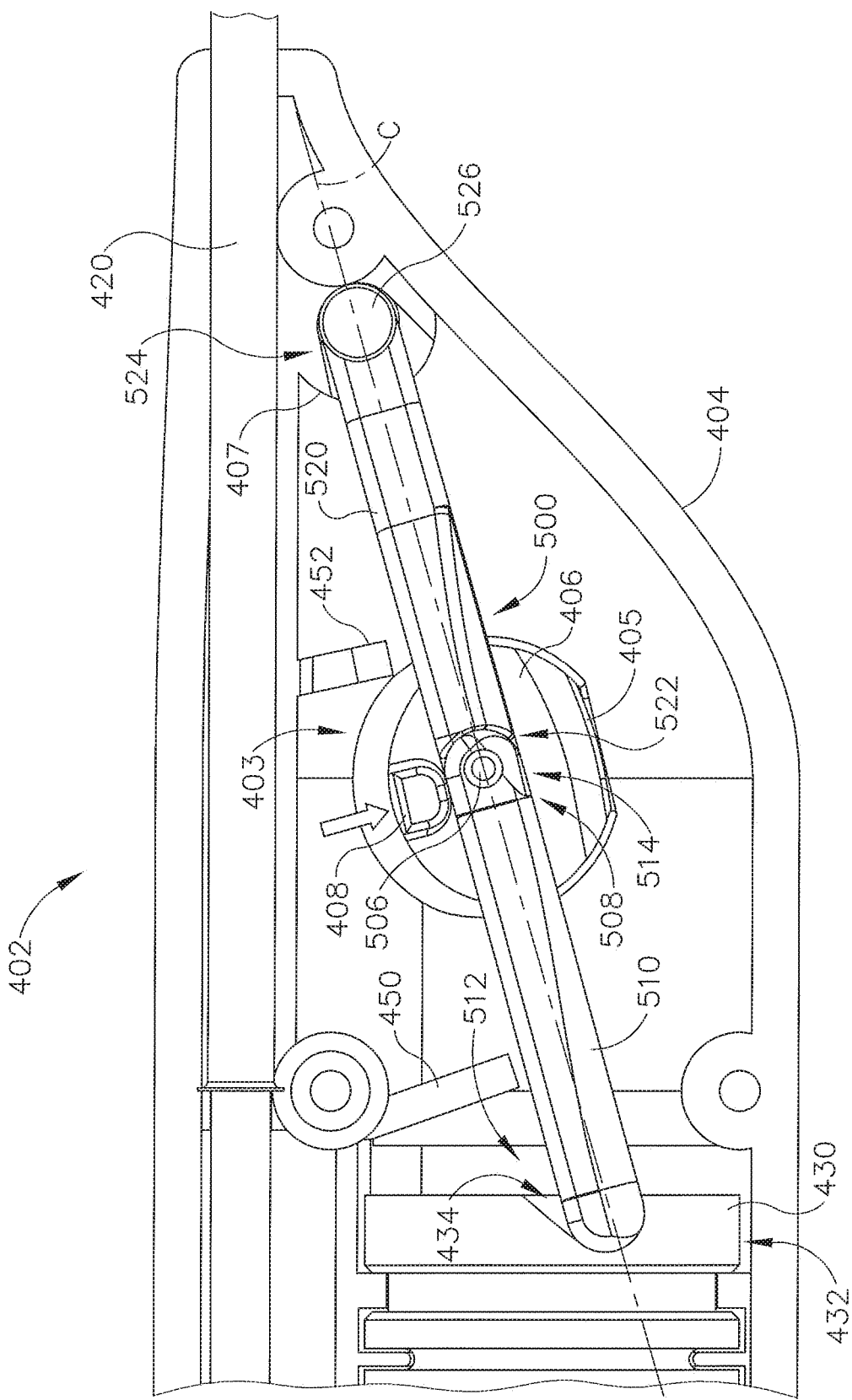
FIG. 24B depicts a side elevational view of the PETDD of FIG. 14 with a housing half omitted, with the integral button of FIG. 21 rotated into a second rotational position, with the collapsible link of FIG. 22 driven into a second position substantially aligned with the centerline of the collapsible link by rotation of the integral button into the second rotational position, and with the rotating cam of FIG. 24A in the locked position.
Figure 25A:
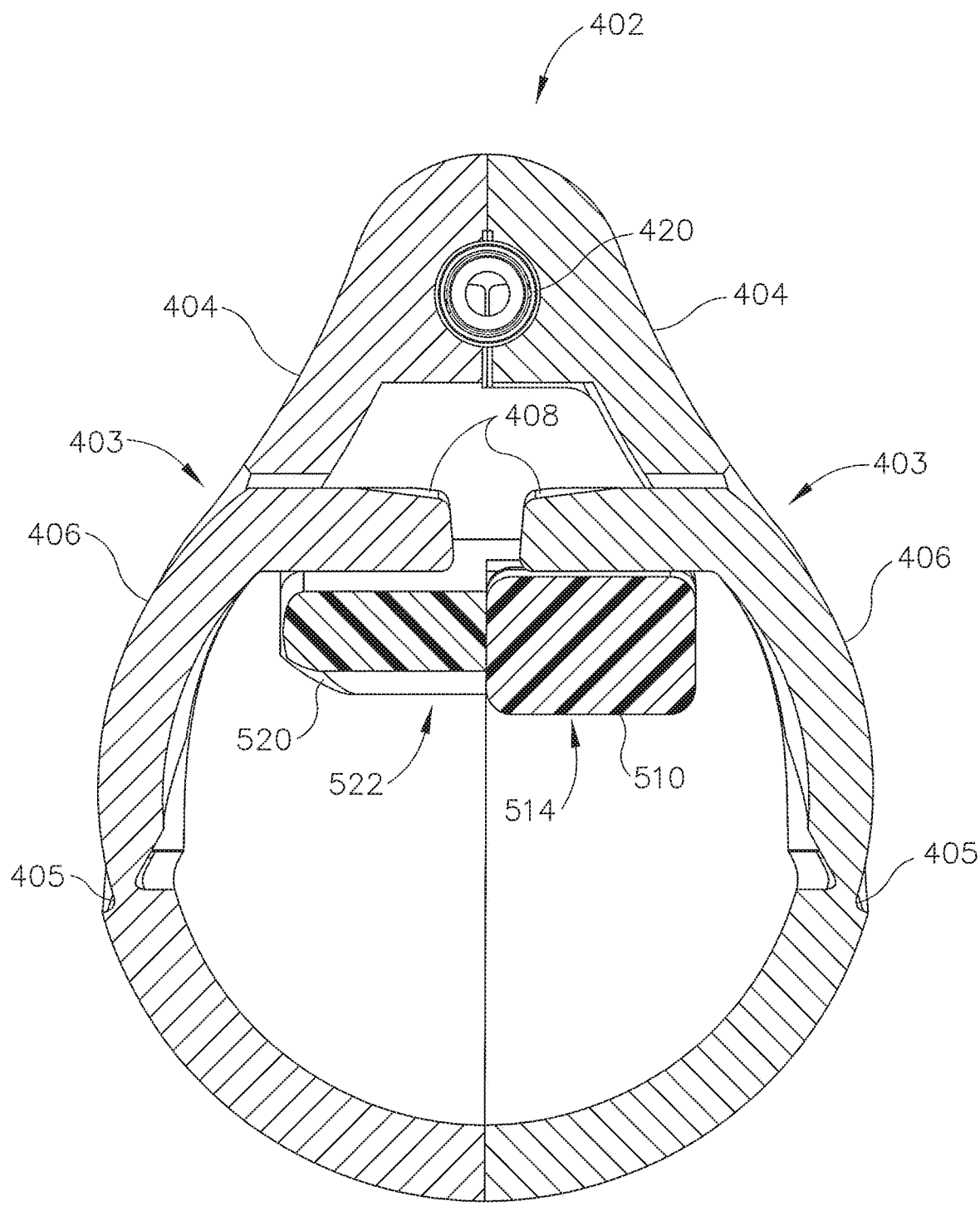
FIG. 25A depicts a cross-sectional rear view of the PETDD of FIG. 14, taken along line 23-23 of FIG. 14, with a housing half omitted, with the integral button of FIG. 21 in a first rotational position, with the collapsible link of FIG. 22 in a first position above a centerline of the collapsible link, and with a rotating cam in a locked position.
Figure 25B:
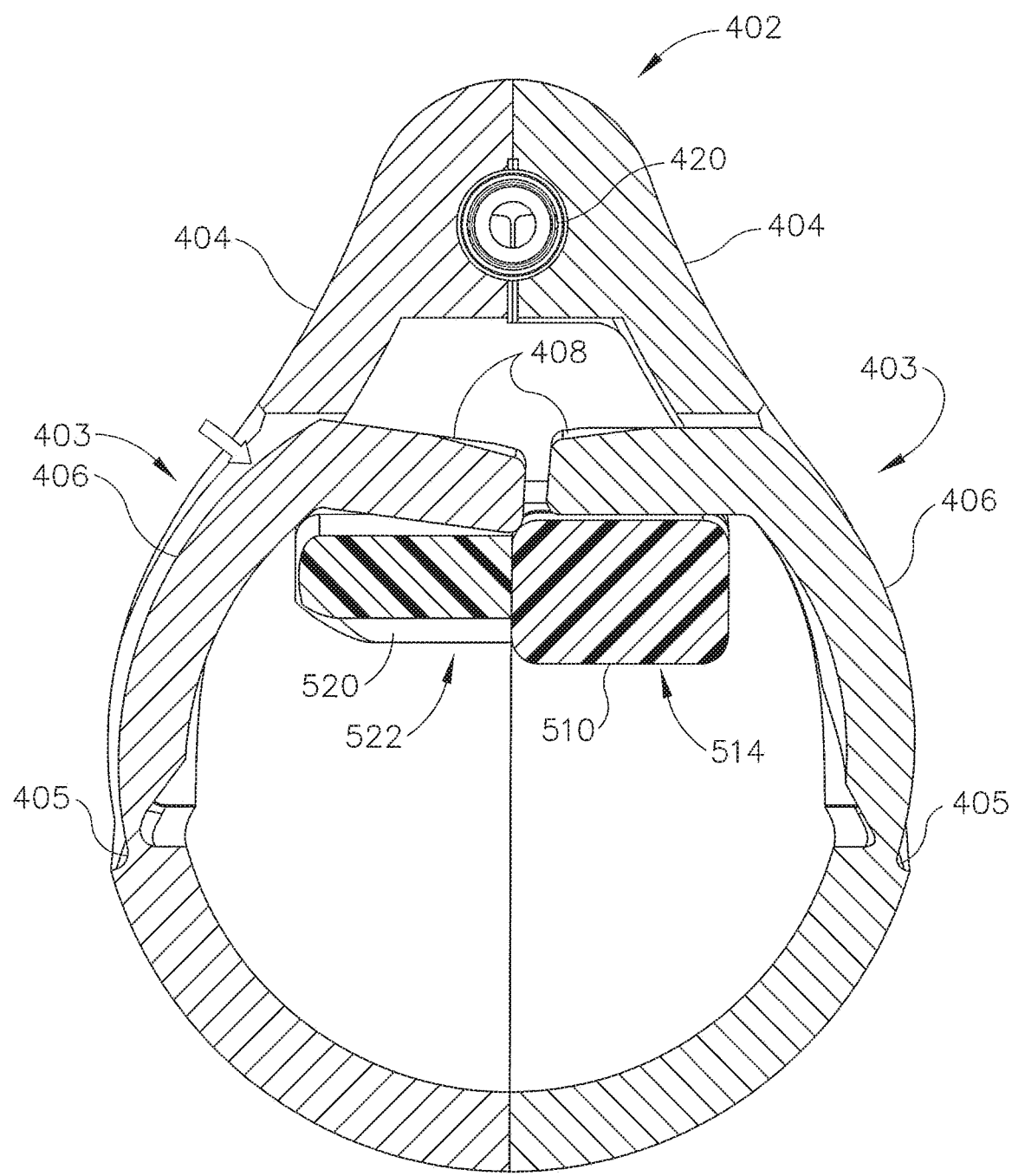
FIG. 25B depicts a cross-sectional rear view of the PETDD of FIG. 14, taken along line 23-23 of FIG. 14, with a housing half omitted, with the integral button of FIG. 21 rotated into a second rotational position, with the collapsible link of FIG. 22 driven into a second position substantially aligned with the centerline of the collapsible link by rotation of the integral button into the second rotational position, and with the rotating cam of FIG. 24A in the locked position.

FIGS. 24B and 25B show collapsible linkage (500) in an "intermediate" position. In this "intermediate" position, collapsible linkage (500) is in a substantially straight configuration with linkage portion (508) substantially aligned coaxially with centerline (C) of collapsible linkage (500). Collapsible linkage (500) is driven into this "intermediate" position by pivoting of pushbutton (406) inwardly such that post (408) of pushbutton (406) engages a top surface of linkage portion (508) of collapsible linkage (500) so as to drive linkage portion (508) downwardly. During this motion, post (408) travels along a plane that is perpendicular to centerline (C); and that passes through pin (506). With collapsible linkage (500) in the intermediate position, proximal end (512), pin (506), and cylindrical projection (526) are all positioned substantially in line with centerline (C). Also in this "intermediate" position, proximal end (512) of first link (510) remains positioned within notch (434) of camshaft (430) to thereby resisting rotation of camshaft (430). It should be understood that camshaft (430) continues to impart an upwardly directed force upon first link (510) via proximal end (512) of first link (510) positioned within notch (434). Collapsible linkage (500) resists this upwardly directed force via post (408) of pushbutton (406) and cylindrical projection (526) of second link (520).

Figure 24C:
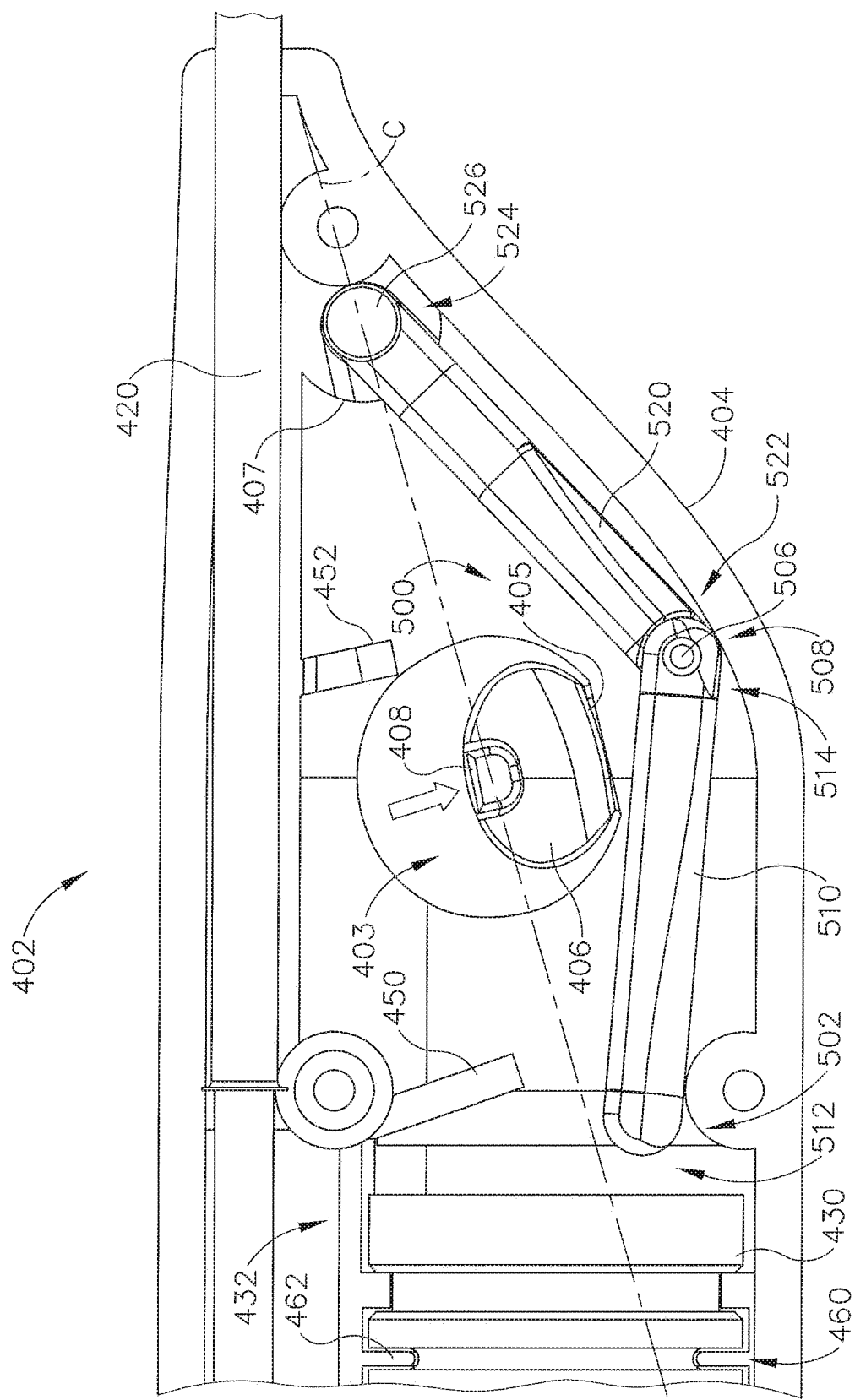
FIG. 24C depicts a side elevational view of the PETDD of FIG. 14 with a housing half omitted, with the integral button of FIG. 21 rotated into a third rotational position, with the collapsible link of FIG. 22 driven into a third (collapsed) position below the centerline of the collapsible link by rotation of the integral button into the third rotational position, and with the rotating cam of FIG. 24A in an unlocked position.
Figure 25C:
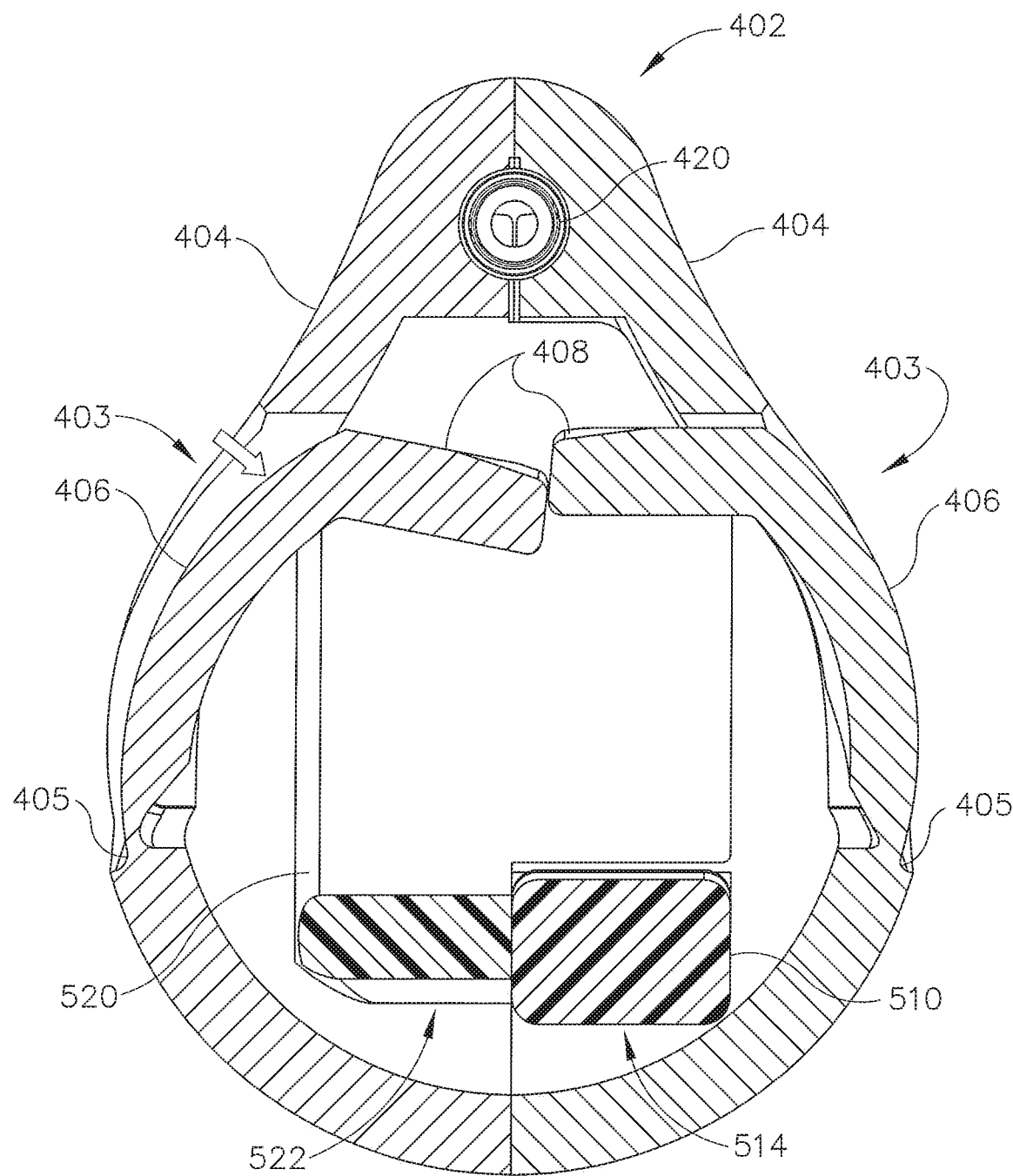
FIG. 25C depicts a cross-sectional rear view of the PETDD of FIG. 14, taken along line 23-23 of FIG. 14, with a housing half omitted, with the integral button of FIG. 21 rotated into a third rotational position, with the collapsible link of FIG. 22 driven into a third (collapsed) position below the centerline of the collapsible link by rotation of the integral button into the third rotational position, and with the rotating cam of FIG. 24A in an unlocked position.

FIGS. 24C and 25C show collapsible linkage (500) in a "collapsed" position. In this "collapsed" position, collapsible linkage (500) is collapsed against an interior surface of housing (404). Collapsible linkage (500) is driven into this "collapsed" position by further pivoting of pushbutton (406) inwardly such that post (408) of pushbutton (406) engages the top surface of linkage portion (508) of collapsible linkage (500) so as to drive linkage portion (508) downwardly below centerline (C). Collapsible linkage (500) is configured to collapse upon linkage portion (508), and pin (506) in particular, being driven below centerline (C). As mentioned above, collapsible linkage (500) is configured such that upon collapsing, proximal end (512) of first link (510) disengages from notch (434) of camshaft (430). Without proximal end (512) of first link (510) to resist rotation of camshaft (430), camshaft (430) rotates thereby actuating PETDD (400). Camshaft (430) provides an actuation sequence in PETDD (400) just like camshaft (130) provides an actuation sequence in PETDD (100) as described above.

B. Exemplary Grease Dampening System

Figure 26:
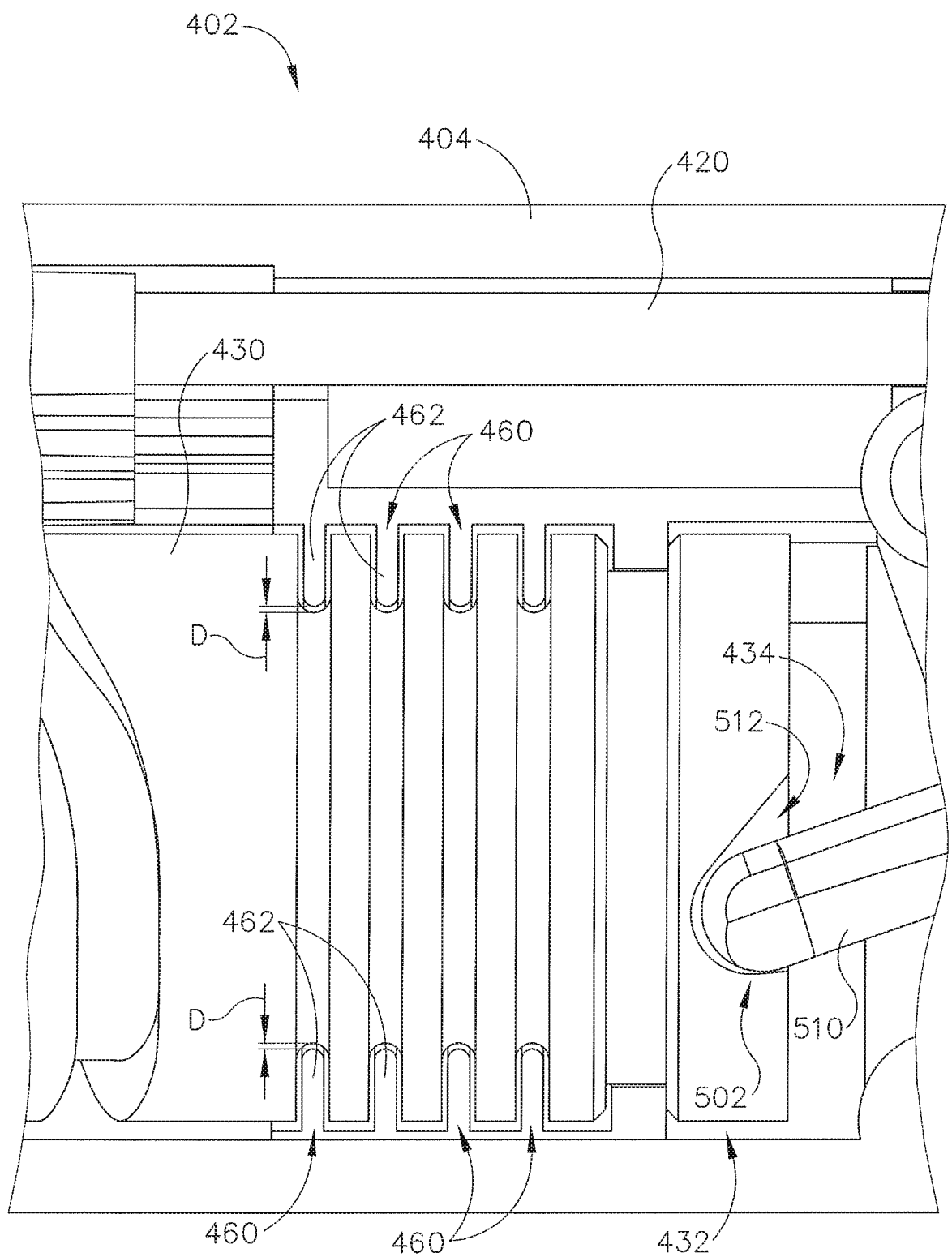
FIG. 26 depicts a side elevational view of a grease space of the PETDD of FIG. 14 with a housing half omitted.

PETDD (400) of the present example further comprises a grease dampening system configured to dissipate energy produced during actuation/operation of PETDD (400). The grease dampening system may further be configured to reduce any noise (e.g., a snapping sound) and/or jerking motion(s) of PETDD (400) upon actuation. By way of example only, a grease dampening system in PETDD (400) may be configured to operate similar to a grease dampening system as disclosed in U.S. Pat. No. 5,497,863, entitled "Rotary Damper," issued Mar. 12, 1996, the disclosure of which is incorporated by reference herein. As best seen in FIG. 26, camshaft (430) of the present example comprises a plurality of annular grooves (460) formed in an exterior surface of camshaft (430) along a distal section of camshaft (430). Housing (404) comprises a plurality of inwardly extending annular projections (462). Grooves (460) of camshaft (430) are configured to receive projections (462) of housing (404) such that as camshaft (430) rotates within housing (404), projections (462) pass within grooves (460). Housing (404) and camshaft (430) are configured such that a constant shear gap distance (D) exists within each groove (460) around the entire circumference of camshaft (430) between grooves (460) and projections (462). Grease is installed and contained within the region of grooves (460). In some versions of PETDD (400), baffles or seals may be included to further contain grease within groves (460). Grease is applied about the full circumference of camshaft (430) such that as camshaft (430) rotates, interaction between grooves (460), projections (462), and the grease continuously and consistently dissipates energy throughout the entirety of rotation of camshaft (430) when PETDD (400) is actuated. Such energy dissipation may increase the steadiness and/or predictability of motion of PETDD (400) during use.

It should be appreciated that the number of groves (460) and/or projections (462) may be increased or decreased to thereby increase or decrease the amount by which rotation of camshaft (430) dissipates energy. Furthermore, gap distance (D) may be increased or decreased to thereby increase or decrease the amount by which rotation of camshaft (430) dissipates energy. Additionally or alternatively, a width of grooves (460) and/or projections (462) may be increased or decreased to thereby increase or decrease the amount by which rotation of camshaft (430) dissipates energy. Finally, the viscosity of the grease may be varied to thereby increase or decrease the amount by which rotation of camshaft (430) dissipates energy.

It should be appreciated that friction inherent in PETDD (400) may dissipate some of the energy produced during actuation/operation of PETDD (400). This inherent friction may vary throughout the actuation sequence of PETDD (400). To account for variations in the inherent friction of PETDD (400), the grease dampening system may be configured such that energy dissipation of the grease dampening system varies throughout the actuation sequence of PETDD (400) so as to complement variations in the inherent friction of PETDD (400) to thereby provide consistent dissipation of energy throughout the entirety of rotation of camshaft (430) when PETDD (400) is actuated. In some versions of PETDD (400), torsion spring (440) and grease dampening system may be combined coaxially along the same portion of PETDD (400).

It should be understood that the foregoing components, features, and operabilities of PETDD (400) are merely illustrative examples. A PETDD (400) may include various other features in addition to or in lieu of those described above. By way of example only, any of the devices herein may also include one or more of the various features disclosed in any of the various references that are incorporated by reference herein.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In some instances, the device is sterilized using conventional ethylene oxide sterilization techniques and systems. In some other instances, the device is placed in a closed and sealed container, such as a plastic or TYVEK bag; and the container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, steam, etc.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
    a handpiece;
    a shaft assembly extending from the handpiece and including a plurality of coaxially arranged shafts;
    a drive assembly configured to drive the plurality of coaxially arranged shafts in a predetermined sequence to deploy a tympanostomy tube;
    a trigger assembly including:
        a linkage including two pivoting links, a first link of the two pivoting links having (i) a first end rotatably coupled to a second link of the two pivoting links, and (ii) a second end releasably engaged with the drive assembly to prevent movement of the drive assembly; and
        a trigger element configured to pivot the two pivoting links to disengage the first link from the drive assembly to activate the drive assembly; and
    a dampening system including a first and second components disposed within an outer surface of the handpiece and configured to contact one another in response to the first link being disengaged from the drive assembly to dissipate energy when the drive assembly drives the plurality of coaxially arranged shafts.

2. The apparatus of claim 1, wherein the handpiece includes a housing,
    the second link including an end rotatably coupled to the housing,
    the two pivoting links are configured to pivot about the end of the second link rotatably coupled to the housing.

3. The apparatus of claim 1, wherein the handpiece includes a housing, the trigger element rotatably coupled to the housing.

4. The apparatus of claim 1, wherein the drive assembly includes a camshaft defining a notch, the camshaft configured to rotate to drive the plurality of coaxially arranged shafts,
    the second end of the first link positionable within the notch to prevent a rotation of the camshaft.

5. The apparatus of claim 1, wherein the handpiece includes a housing including a support component, the support component configured to engage a surface of the linkage to restrict movement of the linkage when the second end of the first link is releasably engaged with the drive assembly.

6. The apparatus of claim 1, wherein the trigger element is configured to pivot the two pivoting links from a first position in which the two pivoting links are bent toward a first direction to a second position in which the two pivoting links are bent toward a second direction opposite to the first direction.

7. An apparatus, comprising:
    a handpiece;
    a shaft assembly extending from the handpiece and including a plurality of coaxially arranged shafts;
    a drive assembly configured to drive the plurality of coaxially arranged shafts in a predetermined sequence to deploy a tympanostomy tube; and
    a trigger assembly including:
        a linkage including two pivoting links, a first link of the two pivoting links releasably engaged with the drive assembly to prevent movement of the drive assembly; and
        a trigger element configured to pivot the linkage to disengage the first link from the drive assembly such that the drive assembly drives the plurality of coaxially arranged shafts in the predetermined sequence to deploy the tympanostomy tube.

8. The apparatus of claim 7, wherein the trigger element is configured to pivot the linkage from a first position in which the two pivoting links are bent toward a first direction to an over-center collapsed position in which the two pivoting links are bent toward a second direction opposite to the first direction.

9. The apparatus of claim 7, wherein the trigger element is configured to pivot the linkage from a first position in which a portion of the linkage is disposed on a first side of a centerline of the linkage past a second position in which the portion of the linkage is aligned with the centerline to an over-center collapsed position in which the portion of the linkage is disposed on a second side of the centerline, the centerline defined as a line extending from a first end of the linkage to a second end of the linkage.

10. The apparatus of claim 7, wherein the trigger element is configured to pivot the linkage from a first position in which the two pivoting links are biased in a first direction to an over-center collapsed position in which the two pivoting links are not biased in the first direction.

11. The apparatus of claim 7, wherein the handpiece includes a housing, the trigger element rotatably coupled to the housing.

12. The apparatus of claim 7, wherein the handpiece includes a housing including a support component, the support component configured to engage a surface of the linkage to restrict movement of the linkage when the first link is releasably engaged with the drive assembly.

13. The apparatus of claim 7, further comprising a dampening system including a first component disposed within the handpiece and a second component formed in the handpiece, one of the first component or the second component configured to receive the other of the first component or the second component such that an interaction between the first component and the second component dissipates energy from the drive assembly when the drive assembly drives the plurality of coaxially arranged shafts.

14. An apparatus, comprising:
a handpiece;
a shaft assembly extending from the handpiece and including a plurality of coaxially arranged shafts;
a drive assembly configured to drive the plurality of coaxially arranged shafts in a predetermined sequence to deploy a tympanostomy tube; and
a trigger assembly including:
a linkage including two pivoting links, a first link of the two pivoting links releasably engaged with the drive assembly to prevent movement of the drive assembly; and
a trigger element configured to move in a direction having a non-zero angle with respect to a plane including the two pivoting links to cause the two pivoting links to pivot relative to each other within the plane such that the first link disengages from the drive assembly.

15. The apparatus of claim 14, wherein the trigger element includes a living hinge, the trigger element configured to pivot about the living hinge.

16. The apparatus of claim 14, wherein the first link is rotatably coupled to a second link of the two pivoting link at a pivot point, the trigger element including a portion configured to engage the linkage at the pivot point.

17. The apparatus of claim 14, wherein the handpiece includes a housing, the trigger element integrally formed with the housing.

18. The apparatus of claim 14, wherein the handpiece includes a housing, the trigger element rotatably coupled to the housing via a pin.

19. The apparatus of claim 14, wherein the trigger element is a first trigger element,
the handpiece including a housing, the housing including a first housing portion and a second housing portion,
the first trigger element rotatably coupled to the first housing portion,
the trigger assembly further comprising a second trigger element rotatably coupled to the second housing portion, the second trigger element configured to pivot about a third axis different from the first axis.

20. The apparatus of claim 7, wherein the drive assembly includes a spring configured to apply a biasing force to a camshaft to drive the plurality of coaxially arranged shafts,
the first link configured to resist movement of the camshaft in response to the biasing force when the first link is engaged with the drive assembly,
the trigger element configured to pivot the linkage to disengage the first link from the drive assembly such that the camshaft moves in response to the biasing force to drive the plurality of coaxially arranged shafts.

* * * * *